US006967201B1

(12) United States Patent  
Briner et al.

(10) Patent No.: US 6,967,201 B1
(45) Date of Patent: *Nov. 22, 2005

(54) BENZOFURYLPIPERAZINES AND BENZOFURYLHOMOPIPERAZINES: SEROTONIN AGONISTS

(75) Inventors: Karin Briner, Indianapolis, IN (US); Joseph Paul Burkhart, Plainfield, IN (US); Timothy Paul Burkholder, Carmel, IN (US); Brian Eugene Cunningham, Martinsville, IN (US); Matthew Joseph Fisher, Mooresville, IN (US); William Harlan Gritton, Zionsville, IN (US); Shawn Christopher Miller, Noblesville, IN (US); Jeffrey Thomas Mullaney, Indianapolis, IN (US); Matthew Robert Reinhard, Indianapolis, IN (US); Dennis Charles Thompson, Indianapolis, IN (US); Leonard Larry Winneroski, Greenwood, IN (US); Yanping Xu, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/031,312

(22) PCT Filed: Jul. 21, 2000

(86) PCT No.: PCT/US00/19543

§ 371 (c)(1),
(2), (4) Date: May 6, 2002

(87) PCT Pub. No.: WO01/09111

PCT Pub. Date: Feb. 8, 2001

Related U.S. Application Data

(60) Provisional application No. 60/146,270, filed on Jul. 29, 1999.

(51) Int. Cl.⁷ .................... A61K 31/496; C07D 405/10
(52) U.S. Cl. .................... 514/254.11; 544/376; 544/231
(58) Field of Search ............... 544/376, 231; 514/254.11

(56) References Cited

U.S. PATENT DOCUMENTS

| 5,698,766 A | 12/1997 | Julius et al. |
| 6,638,936 B1 * | 10/2003 | Briner et al. |

FOREIGN PATENT DOCUMENTS

| EP | 0 006 524 A | 1/1980 |
| EP | 0 189 612 A | 8/1986 |
| WO | WO 95 11243 A | 4/1995 |
| WO | WO 97 08167 A | 3/1997 |
| WO | WO 97 36893 A | 10/1997 |

OTHER PUBLICATIONS

Kuipers W. et al: "N4-unsubstituted 1-6 nl-arylpiperazines as high-affinity 5-HT1A recept r ligands" Journal of Medicinal Chemistry., vol. 38, No. 11, May 26, 1995, pp. 1942-1954, XP002153536 American Chemical Society. Washington., US ISSN: 0022-2623.

* cited by examiner

Primary Examiner—Emily Bernhardt
(74) Attorney, Agent, or Firm—R. Craig Tucker

(57) ABSTRACT

The present invention provides serotonergic benzofurylpiperazines of Formula I:

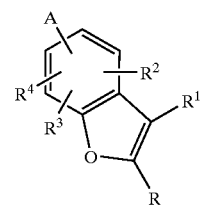

where:
A is a piperazine of formula:

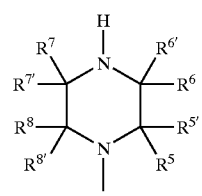

and R, $R^1$, $R^2$, $R^3$, $R^4$, $R^5$, $R^{5'}$, $R^6$, $R^{6'}$, $R^7$, $R^{7'}$, $R^8$, and $R^{8'}$ are as described in the specification.

9 Claims, No Drawings

BENZOFURYLPIPERAZINES AND BENZOFURYLHOMOPIPERAZINES: SEROTONIN AGONISTS

This U.S. national stage application of International Application PCT/US00/19543, filed Jul. 21, 2000, claims priority to U.S. provisional application Ser. No. 60/146,270, filed Jul. 29, 1999.

The neurotransmitter serotonin (5-hydroxytryptamine, 5-HT) has a rich pharmacology arising from a heterogeneous population of at least seven receptor classes. The serotonin 5-HT$_2$ class is further subdivided into at least three subtypes, designated 5-HT$_{2a}$, 5-HT$_{2b}$, and 5-HT$_{2c}$. The 5-HT$_{2c}$ receptor has been isolated and characterized (Julius, et al., U.S. Pat. No. 4,985,352), and transgenic mice lacking the 5-HT$_{2c}$ receptor have been reported to exhibit seizures and an eating disorder resulting in increased consumption of food (Julius, et al., U.S. Pat. No. 5,698,766). Compounds selective for the 5-HT$_{2c}$ receptor would provide useful therapies for the treatment of seizure and eating disorders without the side effects associated with current therapies.

The present invention provides compounds of Formula I:

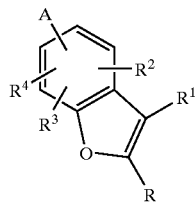

where:

A is homopiperazine or a piperazine of formula:

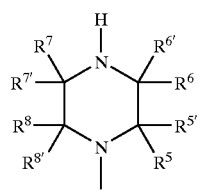

R is hydrogen, halo, trifluoromethyl or $C_1$–$C_6$ alkyl;

R$^1$ is hydrogen, halo, trifluoromethyl, phenyl, or $C_1$–$C_6$ alkyl;

R$^2$, R$^3$, and R$^4$ are independently hydrogen, halo, dihalomethyl, trifluoromethyl, 1,1-difluoroethy-1-yl, cyano, $C_1$–$C_4$ alkoxy, $C_1$–$C_4$ alkoxycarbonyl, $C_1$–$C_6$ alkyl, —C(O)NHR$^9$, or $C_1$–$C_6$ alkyl substituted with a substituent selected from the group consisting of halo, $C_1$–$C_4$ alkoxy and hydroxy.

R$^5$, R$^6$, R$^7$, and R$^8$ are independently hydrogen, $C_1$–$C_6$ alkyl, phenyl, benzyl, hydroxymethyl, halomethyl, dihalomethyl, trihalomethyl, or benzyloxymethyl;

R$^{5'}$ is hydrogen or methyl, provided that R$^{5'}$ may be methyl only when R$^5$ is other than hydrogen; or R$^5$ and R$^{5'}$, together with the carbon atom to which they are attached, form a cyclopropyl moiety;

R$^{6'}$ is hydrogen or methyl, provided that R$^{6'}$ may be methyl only when R$^6$ is other than hydrogen; or R$^6$ and R$^{6'}$, together with the carbon atom to which they are attached, form a cyclopropyl moiety;

R$^{7'}$ is hydrogen or methyl, provided that R$^{7'}$ may be methyl only when R$^7$ is other than hydrogen; or R$^7$ and R$^{7'}$, together with the carbon atom to which they are attached, form a cyclopropyl moiety;

R$^{8'}$ is hydrogen or methyl, provided that R$^{8'}$ may be methyl only when R$^8$ is other than hydrogen; or R$^8$ and R$^{8'}$, together with the carbon atom to which they are attached, form a cyclopropyl moiety;

R$^9$ is $C_1$–$C_8$ alkyl where the alkyl chain is optionally substituted with a substituent selected from the group consisting of phenyl and pyridyl;

or pharmaceutically acceptable acid addition salts thereof subject to the following provisos:

a) when R$^2$, R$^3$, and R$^4$ are all selected from the group consisting of hydrogen, trifluoromethyl, cyano, $C_1$–$C_4$ alkoxy, or $C_1$–$C_4$ alkyl, neither R$^6$ nor R$^7$ may be selected from the group consisting of hydrogen and $C_1$–$C_6$ alkyl unless:
 1. R is halo;
 2. R$^1$ is halo or phenyl
 3. R$^{6'}$ or R$^{7'}$ is methyl; or
 4. R$^5$ or R$^8$ are other than hydrogen, b) when R, R$^1$, and two of R$^2$, R$^3$, and R$^4$ are hydrogen and one of R$^2$, R$^3$, or R$^4$ is selected from the group consisting of fluoro, chloro, bromo, methyl, or methoxy, at least one of R$^5$, R$^6$, R$^7$, or R$^8$ must be other than hydrogen;

c) when R$^1$ is bromo or R is methyl, at least one of R$^2$, R$^3$, and R$^4$ must be other than hydrogen; and d) no more than two of R$^5$, R$^6$, R$^7$, and R$^8$ may be other than hydrogen.

This invention also provides a pharmaceutical formulation which comprises, in association with a pharmaceutically acceptable carrier, diluent or excipient, a compound of Formula I.

The present invention provides a method for increasing activation of the 5-HT$_{2C}$ receptor in mammals comprising administering to a mammal in need of such activation a pharmaceutically effective amount of a compound of Formula I.

The present invention also provides a method for treating obesity in mammals comprising administering to a mammal in need of such treatment a pharmaceutically effective amount of a compound of Formula I.

A further embodiment of this invention is a method for increasing activation of the 5-HT$_{2C}$ receptor for treating a variety of disorders which have been linked to decreased neurotransmission of serotonin in mammals. Included among these disorders are depression, obesity, bulimia, premenstrual syndrome or late luteal phase syndrome, alcoholism, tobacco abuse, panic disorder, anxiety, post-traumatic syndrome, memory loss, dementia of aging, social phobia, attention deficit hyperactivity disorder, disruptive behavior disorders, impulse control disorders, borderline personality disorder, obsessive compulsive disorder, chronic fatigue syndrome, premature ejaculation, erectile difficulty, anorexia nervosa, disorders of sleep, autism, anxiety, seizure disorders, and mutism. Any of these methods employ a compound of Formula I.

This invention also provides the use of a compound of Formula I for the manufacture of a medicament for the treatment of obesity. Additionally, this invention provides a pharmaceutical formulation adapted for the treatment of obesity containing a compound of Formula I. Furthermore, this invention includes a method for the treatment of obesity which comprises administering an effective amount of a compound of Formula I.

The general chemical terms used in the formulae above have their usual meanings. For example, the term "alkyl" includes such groups as methyl, ethyl, n-propyl, isopropyl, butyl, isobutyl, sec-butyl, tert-butyl, and the like. The term "alkoxy" includes methoxy, ethoxy, propoxy, isopropoxy, butoxy and the like. The term "acyl" includes such groups as formyl, acetyl, propionyl, butyryl, 2-methylpropionyl, and the like. The term "halo" includes fluoro, chloro, bromo and iodo.

The term "$C_1$–$C_6$ alkyl substituted with a substituent selected from the group consisting of $C_1$–$C_4$ alkoxy and hydroxy" means a branched or linear alkyl group substituted in the carbon chain with one or two substituents independently selected from hydroxy or $C_1$–$C_4$ alkoxy.

The term "$C_1$–$C_8$ alkyl where the alkyl chain is optionally substituted with a substituent selected from the group consisting of phenyl and pyridyl" means a branched or linear alkyl group which may be substituted in the carbon chain with a phenyl or pyridinyl ring.

Since the compounds of this invention are amines, they are basic in nature and accordingly react with any of a number of inorganic and organic acids to form pharmaceutically acceptable acid addition salts. Since some of the free amines of the compounds of this invention are typically oils at room temperature, it is preferable to convert the free amines to their pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogen-phosphate, dihydrogenphosphate, metaphosphate, pyro-phosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid and fumaric acid.

The skilled artisan will appreciate that certain of the compounds of the present invention have at least one chiral carbon, and may therefore exist as a racemate, as individual enantiomers or diastereomers, and as mixtures of individual enantiomers or diastereomers. For example, individual enantiomers of compounds of the invention where one substituent on the piperazine ring is other than hydrogen are illustrated by the following structures:

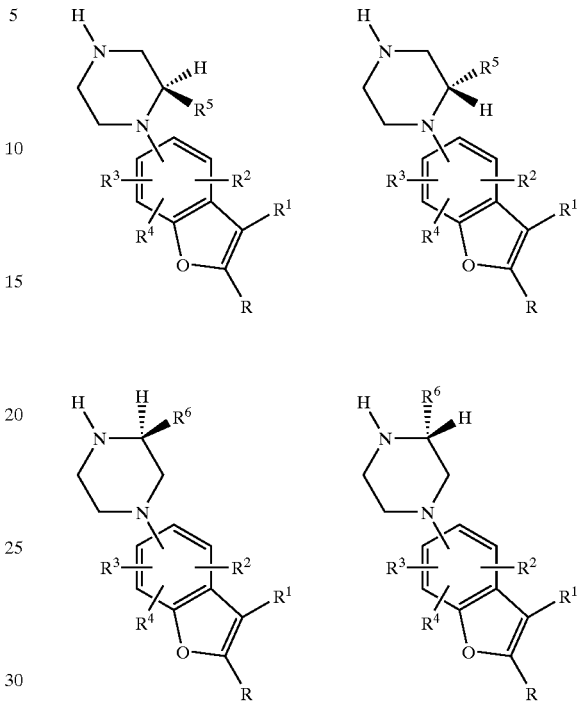

Individual diastereomers, for example those compounds of the present invention where two substituents on the piperazine ring are other than hydrogen, are illustrated by the following structures:

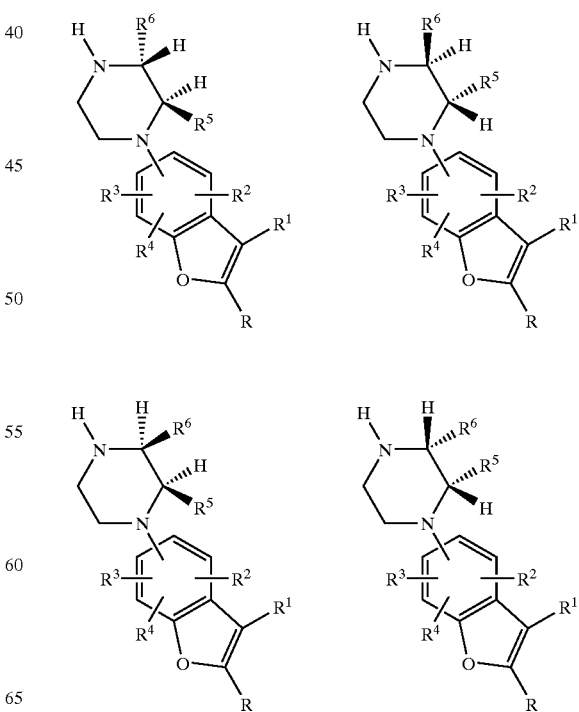

The enantiomers and diastereomers illustrated above are representative of other enantiomers and diasteromeric pairs created by other combinations of non-hydrogen substituents on the piperazine ring, and are not intended to limit the scope of the present invention in any way. Furthermore, the skilled artisan will appreciate that certain substituents on the benzofuryl ring of the compounds of the invention introduce additional asymmetric centers into the molecule, creating additional optical isomers as described above.

While it is a preferred embodiment of the invention that the compounds of the invention exist, are formulated, and are used as single enantiomers or diastereomers, the present invention also contemplates the compounds of the invention existing in racemic form and as mixtures of the individual enantiomers and diastereomers. The methods and formulations of the invention also contemplate the use and formulation of the compounds of the invention in their racemic form and as mixtures of the individual enantiomers and diastereomers.

The individual enantiomers and diastereomers may be prepared by chiral chromatography of the racemic or enantiomerically or diastereomerically enriched free amine, or fractional crystallization of salts prepared from racemic or enantiomerically or diastereomerically enriched free amine and a chiral acid. Alternatively, the free amine may be reacted with a chiral auxiliary and the enantiomers or diastereomers separated by chromatography followed by removal of the chiral auxiliary to regenerate the free amine. Furthermore, separation of enantiomers or diastereomers may be performed at any convenient point in the synthesis of the compounds of the invention. The compounds of the invention may also be prepared by the use of chiral syntheses.

While all of the compounds of Formula I are useful 5-$HT_{2c}$ agonists, certain classes of the compounds are preferred. The following paragraphs describe such preferred classes:

aa) A is a piperazine of formula (i);
ab) A is attached at either the 4- or 7-position of the benzofuran ring;
ac) A is attached at the 4-position of the benzofuran ring;
ad) A is attached at the 7-position of the benzofuran ring;
ae) R is hydrogen;
af) R is halo;
ag) R is $C_1$–$C_6$ alkyl;
ah) $R^1$ is hydrogen;
ai) $R^1$ is halo;
aj) $R^1$ is trifluoromethyl;
ak) $R^1$ is $C_1$–$C_6$ alkyl;
al) $R^2$ is hydrogen;
am) $R^2$ is halo;
an) $R^2$ is fluoro;
ao) $R^2$ is —C(O)$NHR^9$;
ap) $R^2$ is trifluoromethyl;
aq) $R^3$ is hydrogen;
ar) $R^3$ is halo;
as) $R^3$ is fluoro;
at) $R^3$ is —C(O)$NHR^9$;
au) $R^3$ is trifluoromethyl;
av) $R^4$ is hydrogen;
aw) $R^4$ is halo;
ax) $R^4$ is fluoro;
ay) $R^4$ is —C(O)$NHR^9$;
az) $R^4$ is trifluoromethyl;
ba) $R^5$ is hydrogen;
bb) $R^5$ is $C_1$–$C_4$ alkyl;
bc) $R^5$ is methyl;
bd) $R^6$ is hydrogen;
be) $R^6$ is $C_1$–$C_4$ alkyl;
bf) $R^6$ is methyl;
bg) $R^7$ is hydrogen;
bh) $R^7$ is $C_1$–$C_4$ alkyl;
bi) $R^7$ is methyl;
bj) $R^8$ is hydrogen;
bk) $R^8$ is $C_1$–$C_4$ alkyl;
bl) $R^8$ is methyl;
bm) $R^5$ and $R^{5'}$ taken together with the carbon to which they are attached form a cyclopropyl moiety;
bn) $R^6$ and $R^{6'}$ taken together with the carbon to which they are attached form a cyclopropyl moiety;
bo) $R^7$ and $R^{7'}$ taken together with the carbon to which they are attached form a cyclopropyl moiety;
bp) $R^8$ and $R^{8'}$ taken together with the carbon to which they are attached form a cyclopropyl moiety;
bq) The compound is a free base;
br) The compound is a salt;
bs) The compound is the hydrochloride salt;
bt) The compound is the fumarate salt;
bu) The compound is a racemate;
bv) The compound is a single enantiomer;
bw) The compound is a single diastereomer;
bx) A is attached at the 7-position of the benzofuryl moiety and only one of $R^2$, $R^3$, or $R^4$ is hydrogen;
by) A is attached at the 7-position of the benzofuryl moiety and all three of $R^2$, $R^3$, and $R^4$ are other than hydrogen;
bz) One of $R^5$, $R^6$, $R^7$, and $R^8$ is other than hydrogen;
ca) Two of $R^5$, $R^6$, $R^7$, and $R^8$ are other than hydrogen;
cb) A is a piperazine of formula (i) and it is substituted in both the two and five positions;
cc) A is a piperazine of formula (i) and it is substituted in both the two and three positions;
cd) A is a piperazine of formula (i) and it is substituted in the two position.

It will be understood that the above classes may be combined to form additional preferred classes.

The present invention also provides a method for increasing activation of the 5-$HT_{2C}$ receptor in mammals by administering to a mammal in need of such activation a pharmaceutically effective amount of a compound of Formula II. The preferred mammal is human.

The compounds of the invention are prepared beginning with an appropriately substituted benzofuran as illustrated in the following scheme where X is bromo, iodo, or trifluoromethylsulfonyloxy; PG is a nitrogen protecting group; and the variables R, $R^1$, $R^2$, $R^3$, $R^4$, $R^5$, and $R^6$ are as previously defined:

Synthetic Scheme I

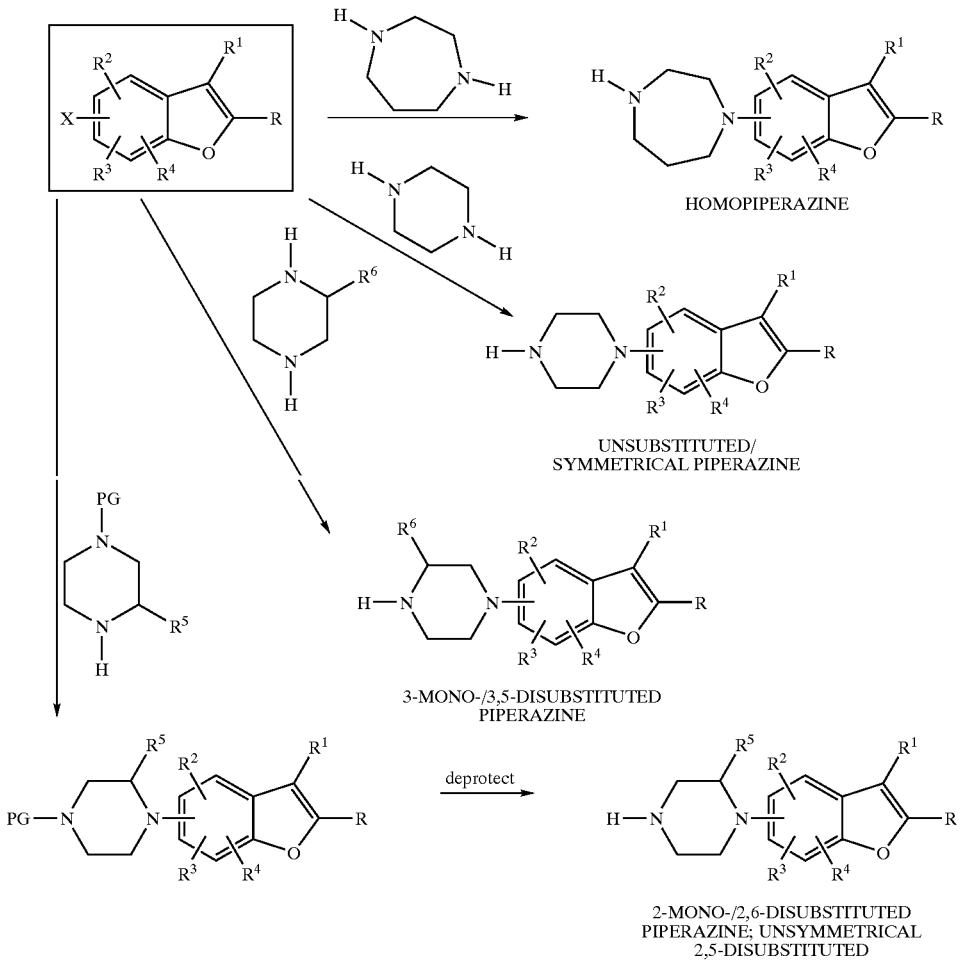

Generally, a benzofuryl bromide, iodide, or triflate is reacted with homopiperazine or an appropriate piperazine in the presence of an appropriate catalyst and base. Typically, 1–10 equivalents of homopiperazine or an appropriate piperazine relative to beginning benzofuran are employed. The coupling is catalyzed with an appropriate metal catalyst, such as nickel or palladium. Palladium catalysts are preferred and are either commercially available or may be generated in situ by combining trisdibenzylideneacetone dipalladium or palladium chloride with a phosphine ligand such as racemic 2,2'-bis(diphenylphosphino)-1,1'-binaphthyl, tri-o-tolylphosphine, or bis(diphenylphosphino)ferrocene. The ratio of palladium to phosphine ligand is typically between 1:1 and 1:5. Typically 0.01 to 0.1 equivalents of catalyst are used relative to starting benzofuran. Useful bases include sodium tert-butoxide, lithium tert-butoxide, and potassium tert-butoxide. Typically 1–5 equivalents of base are used relative to starting benzofuran.

The benzofuran, homopiperazine or appropriate piperazine, catalyst, and base are combined in a suitable solvent. Suitable solvents include toluene, benzene, dioxane, and tetrahydrofuran. The mixture is stirred at 20–200° C. under an inert atmosphere, typically nitrogen or argon, until the reaction is complete. Additional portions of any reagent may be added during the course of the reaction as necessary or desired.

When homopiperazine, piperazine, or a symmetrically substituted piperazine is reacted with a benzofuran, 3.5–4 equivalents of the appropriate amine are used to avoid coupling a benzofuran moiety at each available nitrogen. When an unsymmetrically substituted piperazine is employed in the coupling to provide, for example, 3-mono- or 3,5-disubstituted piperazine products, the least sterically hindered nitrogen reacts selectively, requiring the use of only 1–1.2 equivalents of the amine. When the desired product results from coupling at the most sterically hindered nitrogen, for example to provide 2-mono- or 2,6-disubstituted piperazine products, the least hindered nitrogen must be protected. Nitrogen protecting groups useful for this reaction are well known to the skilled artisan. A summary of such groups may be found in Greene's *Protective Groups in Organic Synthesis*, Second Edition, Wiley Interscience. Particularly useful protecting groups include benzyl and tert-butoxycarbonyl. Once the protected piperazine has been coupled with the benzofuran, the protecting group is removed by standard methods. The benzyl moiety, for example, may be removed by either hydrogenation or treatment with 1-chloroethyl chloroformate. The tert-butoxycarbonyl moiety may be removed by treatment with acid, for example, trifluoroacetic acid or hydrogen chloride.

Compounds of the invention may alternatively be prepared as described in the following scheme where variables R, $R^1$, $R^2$, $R^3$, $R^4$, $R^5$, and $R^6$ are as previously defined:

benzyloxyethylamine under the conditions previously described. The skilled artisan will appreciate that the appropriately substituted benzyloxyethylamines may be prepared from the corresponding amino acid under standard conditions. The resulting ether is deprotected and the correspond- Synthetic Scheme II

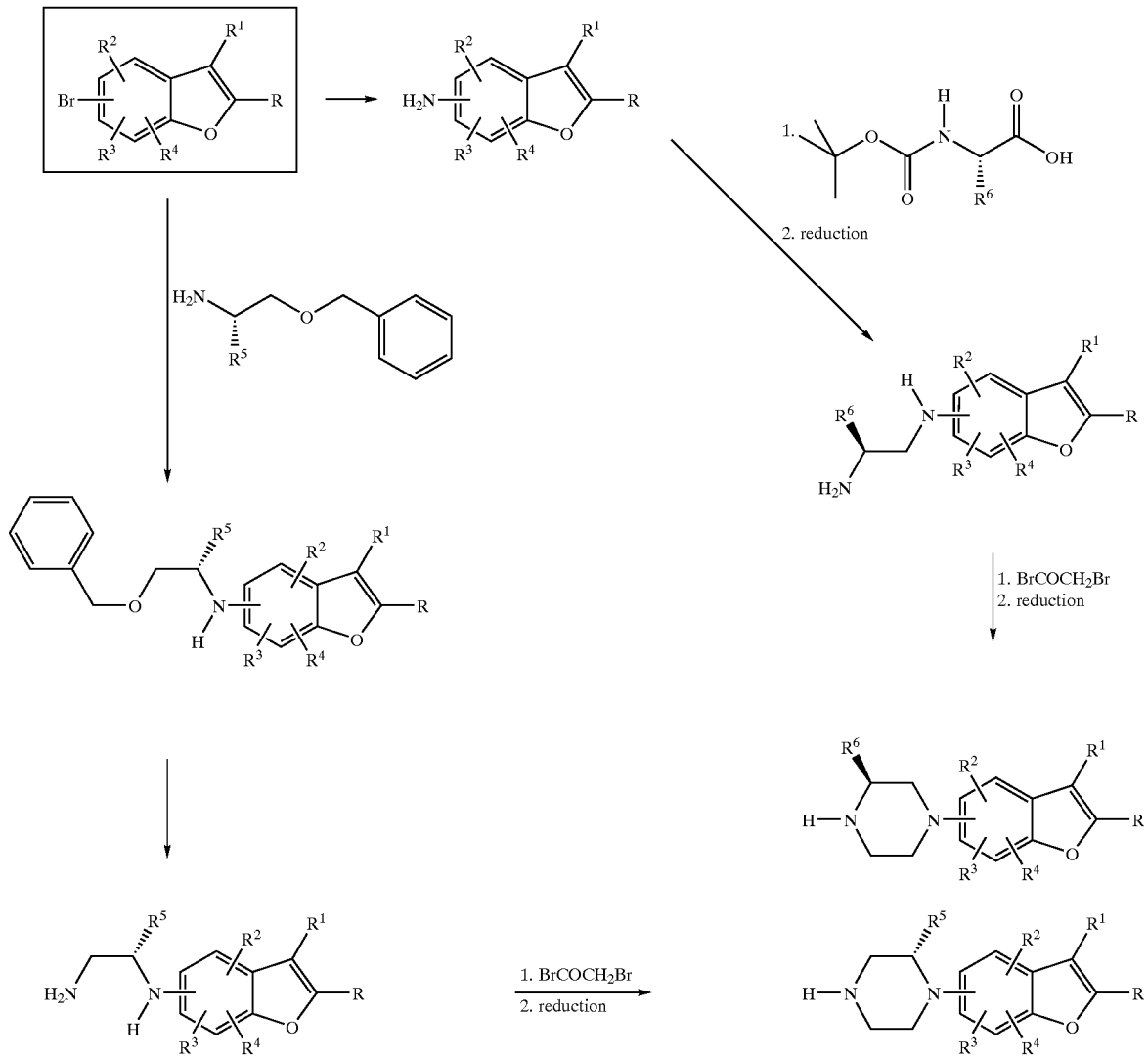

The piperazine ring may be constructed onto the benzofuryl moiety by coupling an appropriate benzofuran, for example a bromobenzofuran, with benzophenone imine under the coupling conditions previously described. The resulting adduct is treated with aqueous acid to provide the corresponding amine. This aminobenzofuran is coupled with an appropriate nitrogen-protected amino acid under standard peptide coupling conditions. The resulting amide is reduced with a hydride reducing agent such as lithium aluminum hydride, and the corresponding amine deprotected to provide a diamine.

Alternatively, an appropriately substituted benzofuran, for example bromobenzofuran, is coupled with an appropriate ing alcohol converted to the diamine under standard conditions.

The diamines prepared by either of these routes is treated with an appropriate reagent, for example bromoacetyl bromide, to prepare the corresponding lactam. Reduction of this lactam under standard hydride reducing conditions, for example by treatment with borane or lithium aluminum hydride, provide the compounds of the present invention.

The requisite benzofuran intermediates are either commercially available or may be prepared from an appropriately substituted phenol by methods well known in the art as illustrated in the following scheme where variables $R^2$, $R^3$, and $R^{12}$ are as previously defined:

Synthetic Scheme III

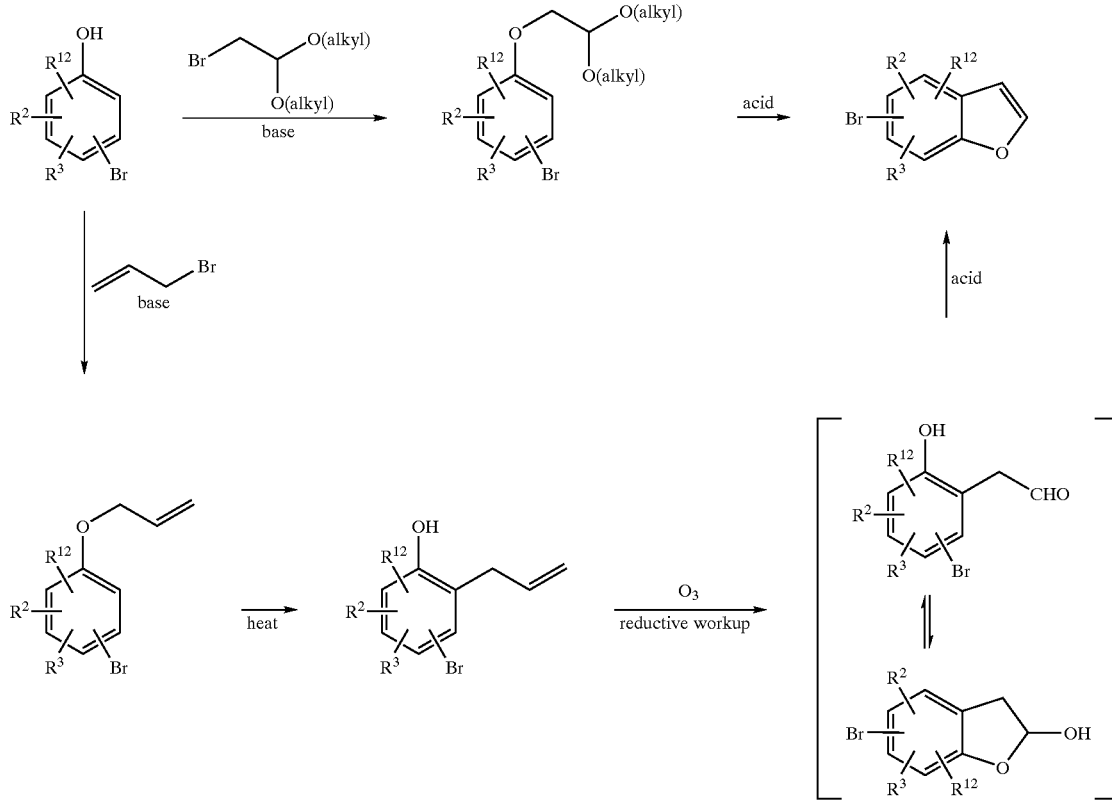

A solution of an appropriately substituted phenol in a suitable solvent, typically dimethylformamide, is treated with a base, to generate the corresponding phenoxide. Bases useful for this reaction include hydride sources, such as sodium or potassium hydride, or carbonates, such as sodium or potassium carbonate. The phenoxide solution is then reacted with a chloro- or bromoacetaldehyde which is protected as a cyclic or dialkyl acetal. Bromoacetaldehyde diethyl acetal is particularly useful for this reaction. The phenoxyacetaldehyde acetal prepared by this procedure is reacted with a source of acid in a suitable solvent to provide the desired benzofuran. Suitable solvents include aromatic solvents such as toluene, xylene, benzene, and halobenzenes such as chlorobenzene. Suitable acids include concentrated sulfuric acid, polyphosphoric acid, and acidic resins such as Amberlyst 15™.

Alternatively, the phenoxide solution is treated with an allyl bromide or allyl chloride to provide, after standard isolation and purification procedures, the corresponding allyl ether. This purified ether is heated at a temperature sufficient to effect an ortho-Claisen rearrangement to provide the corresponding o-allylphenol. It is critical that the allyl ether employed in this rearrangement is substantially free of residual dimethylformamide. The skilled artisan will appreciate that, depending upon the location and nature of the $R^2$ and $R^3$ substituents, the rearrangement can provide a mixture of two isomeric products. These isomers may be separated at this stage or later in the synthetic sequence as is convenient or desired. The separation may be effected by chromatography, distillation, or crystallization. The o-allylphenol is then treated with an excess of ozone in an appropriate solvent, dichloromethane and methanol are useful solvents for this step. The reaction mixture is then purged of ozone and the ozonide is treated under reducing conditions, typically by treatment with triphenylphosphine or dimethylsulfide, to provide the corresponding phenylacetaldehyde. The skilled artisan will appreciate that the orientation of the aldehyde with the respect to the phenolic hydroxyl group gives rise to the formation of a cyclic hemiacetal which exists in some equilibrium mixture with the free hydroxyaldehyde. A solution of this equilibrium mixture in a suitable solvent, such as toluene, is treated with a catalytic amount of an appropriate acid, such as sulfuric acid, to provide the desired benzofuran.

The skilled artisan will appreciate that benzofurans substituted in the 2- and/or 3-position may be prepared by modification of the chemistry described in Synthetic Scheme III. For example, the phenol may be alkylated with a suitable haloketone and then cyclized to provide a substituted benzofuran. Alternatively, the benzofuran moiety may be substituted in the 2- or 3-position at any convenient point in the synthesis of the compounds of the present invention by methods known to those skilled in the art.

The requisite benzofurans may also be prepared from an appropriately substituted phenol as illustrated in the following scheme where variables $R^2$, $R^3$, and $R^{12}$ are as previously defined:

Synthetic Scheme IV

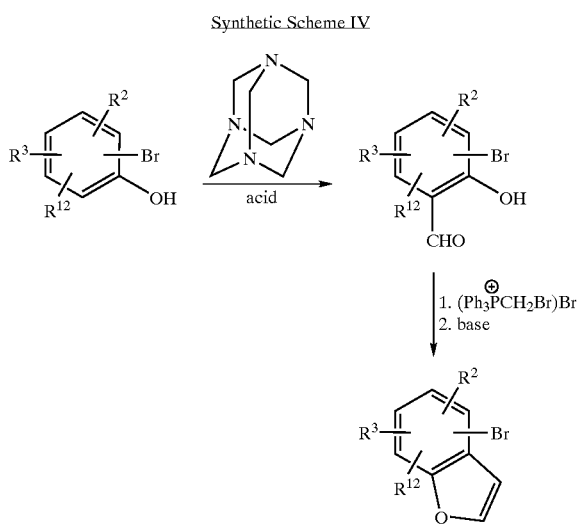

A mixture of an appropriate phenol and hexamethylenetetramine are treated with an appropriate acid, such as trifluoroacetic acid, to provide upon aqueous workup the corresponding o-formylphenol. This o-formylphenol is then treated with (bromomethyl)triphenylphosphonium bromide followed by an appropriate base such as potassium tert-butoxide to provide the desired benzofuran.

The requisite piperazines are either commercially available or may be prepared by methods well known in the art. One such approach is illustrated in the following scheme where $R^5$ is as previously defined:

peptide coupling conditions to provide the corresponding dipeptide. This dipeptide is N-deprotected and heated to provide the corresponding dilactam. This dilactam is reduced under standard hydride reducing conditions, for example with lithium aluminum hydride, to provide the corresponding N-benzylated piperazine. The N-benzyl group is removed by either catalytic hydrogenation or by treatment with 1-chloroethyl chloroformate to provide the corresponding piperazine. The benzyl group may be removed either prior or subsequent to coupling with an appropriate benzofuran depending upon the specific coupling orientation desired as described supra.

The skilled artisan will appreciate that the racemic N-tert-butoxycarbonyl alanine and N-benzyl glycine ethyl ester displayed in Synthetic Scheme V are illustrative, and are not intended to limit the scope of the invention in any way. The amino acids employed in this synthetic scheme are dictated by the specific substituted piperazine desired. Furthermore, the skilled artisan will appreciate that not all substituents are compatible with the reaction conditions employed to prepare the compounds of the invention. Those substituents incompatible with these conditions may be introduced at a more convenient point in the synthesis, or may be prepared by functional group transformations well known to one of ordinary skill in the art. Furthermore, many of the compounds of the present invention, while useful 5-HT$_{2C}$ agonists in their own right, are useful intermediates to prepare other compounds of the invention. Those compounds of the invention bearing an ester functionality, for example, may be hydrolyzed under standard conditions to provide the corresponding carboxylic acids. These acids may then be reacted with amines under standard peptide coupling conditions to provide the corresponding amides. Alternatively, the esters may be reduced to provide the corresponding alcohols.

Synthetic Scheme V

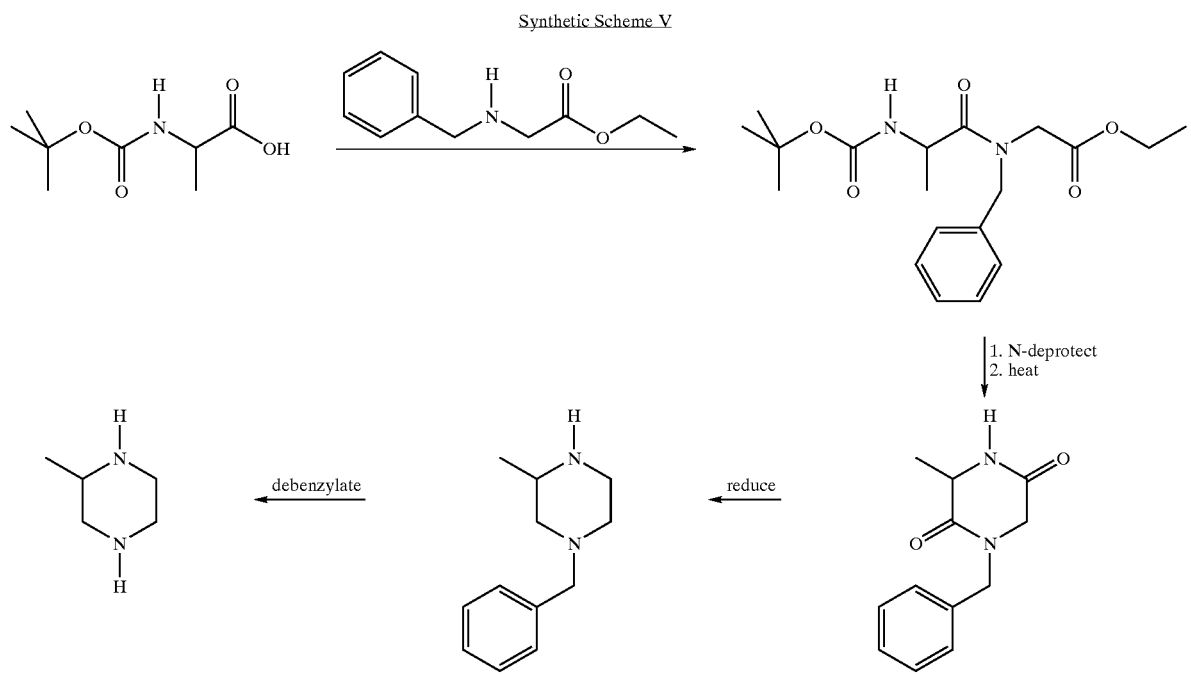

An appropriate N-protected amino acid is coupled with an N-benzylated carboxy-protected amino acid under standard Furthermore, alkoxy groups may be cleaved to provide the corresponding phenols, and primary amines may be diazotized and displaced to provide the corresponding halogenated compounds. Furthermore, an alcohol or aldehyde or ketone may be converted to the corresponding monofluoro or difluoro derivative by reaction with diethylaminosulfur trifluoride at any convenient point on the synthesis of the compounds of the present invention.

The following Preparations and Examples are illustrative of methods useful for the synthesis of the compounds of the present invention.

Preparation I 5-fluoro-7-bromobenzofuran 2-(2-bromo-4-fluorophenoxy)acetaldehyde Diethyl Acetal To a solution of 20 gm (105 mMol) 2-bromo-4-fluorophenol in 211 mL dimethylformamide were added 15.8 mL (105 mMol) bromoacetaldehyde diethyl acetal followed by 14.5 gm (105 mMol) anhydrous potassium carbonate. This mixture was then heated at reflux for about 18 hours under a nitrogen atmosphere. The reaction mixture was then concentrated under reduced pressure and the resulting residue partitioned between 200 mL of ethyl acetate and 200 mL 1N sodium hydroxide. The phases were separated and the ethyl acetate phase was washed with 200 mL of water, giving rise to an emulsion. An additional 100 mL ethyl acetate and 20 mL of water were added to the emulsion. The separated ethyl acetate phase and emulsion were removed and saved. The ethyl acetate phase was washed again with 200 mL of water. This new emulsion was combined with the original emulsion and aqueous phase. The mixture was partitioned between 700 mL ethyl acetate and 780 mL of water. The emulsion and aqueous layer (1600 mL) were removed. The organic phase was dried over magnesium sulfate and concentrated under reduced pressure to provide 26.4 gm (82%) of the desired material as an amber oil. The reserved emulsion and aqueous phase was washed with 1 L of toluene. The phases were separated and organic phase was dried over magnesium sulfate and concentrated under reduced pressure to provide an additional 4.67 gm of the desired compound as an amber oil. Total recovery of desired product was 31.1 gm (96.7%).

Cyclization

A mixture of 109.4 gm Amberlyst-15 in 707 mL chlorobenzene was heated at reflux to remove water by azeotropic distillation. Distillate was removed until the volume remaining in the pot was about 500 mL. To this mixture was then added dropwise over 2 hours a solution of 109.4 gm (356 mMol) 2-(2-bromo-4-fluorophenoxy)acetaldehyde diethyl acetal in 4060 mL chlorobenzene. The mixture was stirred at reflux with constant water removal. When no more water was observed in the azeotrope distillate, the reaction mixture was cooled to room temperature. The filter cake was washed with 400 mL dichloromethane and the combined filtrates were concentrated under reduced pressure to provide 102 gm of a colorless oil. This oil was diluted with 500 mL hexane and subjected to silica gel chromatography, eluting with hexane. Fractions containing the desired product were combined and concentrated under reduced pressure to provide 39.6 gm (52%) of the title compound.

$^1$H-NMR(CDCl$_3$): δ 7.75 (d, J=2.1 Hz, 1H), 7.27 (dd, $J_{H,H}$= 2.5 Hz, $J_{H,F}$=8.8 Hz, 1H), 7.25 (dd, $J_{H,H}$=2.5 Hz, $J_{H,F}$= 8.3 Hz, 1H), 6.85 (d, J=2.2 Hz, 1H).

Preparation II 4-methoxy-7-bromobenzofuran 2-bromo-5-methoxyphenol and 4-bromo-5-methoxyphenol A solution of 40.0 gm (322.2 mMol) 3-methoxyphenol in 1 L acetonitrile was cooled to 0° C. under a nitrogen atmosphere. To this cooled solution was added a solution of 57.35 gm (322.2 mMol) N-bromosuccinimide in 500 mL acetonitrile dropwise at a rate to maintain the temperature of the reaction mixture at 0° C. (approximately 2 hours). The reaction mixture was stirred at 0° C. for about 1 hour after the addition was complete and was then concentrated under reduced pressure. The residue was treated with carbon tetrachloride and the solid which formed was removed by filtration. The filtrate was concentrated under reduced pressure to provide a mixture of bromination isomers as a red oil.

This oil was subjected to silica gel chromatography, eluting with a gradient system of hexane containing from 0–30% ethyl acetate. Fractions containing the fastest eluting compound were combined and concentrated under reduced pressure to provide 18.1 gm (28%) of 2-bromo-5-methoxyphenol as a clear liquid.

$^1$H-NMR(CDCl$_3$): δ 7.31 (d, 1H), 6.6 (d, 1H), 6.41 (dd, 1H), 5.5 (s, 1H), 3.77 (s, 3H).

Fractions containing the later eluting components were combined and concentrated under reduced pressure. This residue was subjected to silica gel chromatography, eluting with dichloromethane. Fractions containing substantially pure 4-bromo-5-methoxyphenol were combined and concentrated under reduced pressure to provide 24.1 gm (37%) of a white crystalline solid (m.p.=68–69° C.).

$^1$H-NMR(CDCl$_3$): δ 7.34 (d, 1H), 6.45 (d, 1H), 6.33 (dd, 1H), 4.9 (br s, 1H), 3.85 (s, 3H).

2-(2-bromo-5-methoxyphenoxy)acetaldehyde Diethyl Acetal

A mixture of 16.0 gm (78.8 mmol) 2-bromo-5-methoxyphenol, 10.9 gm (78.8 mMol) potassium carbonate, and 15.5 gm (78.8 mMol) bromoacetaldehyde diethyl acetal in 300 mL dimethylformamide was heated at 142° C. for 16 hours. The reaction mixture was then cooled to room temperature and diluted with 100 mL 2N sodium hydroxide followed by 500 mL ethyl acetate. This mixture was washed twice with 1 L of water. The combined aqueous washes were extracted twice with 300 mL portions of ethyl acetate. All organic phases were combined, washed with lt of water, washed with 1 L of saturated aqueous sodium chloride, dried over magnesium sulfate and concentrated under reduced pressure to provide the desired compound as a dark amber oil.

Cyclization

A mixture of 17 gm polyphosphoric acid in 500 mL chlorobenzene was heated to 80° C. with stirring. To this mixture was added dropwise over 30 minutes a solution of 16 gm (50.13 mMol) 2-(2-bromo-5-methoxyphenoxy)acetaldehyde diethyl acetal in 100 mL chlorobenzene. The resulting mixture was stirred for 5 hours at 80° C. and 2 hours at 120° C. The reaction mixture was cooled to room temperature and the chlorobenzene solution was decanted from the polyphosphoric acid phase. The remaining residue was washed with five 200 mL portions of diethyl ether. All of the organic phases were combined and concentrated under reduced pressure to provide a dark amber oil. This oil was subjected to silica gel chromatography, eluting with a gradient of hexane containing from 0–5% ethyl acetate.

Fractions containing product were combined and concentrated under reduced pressure to provide 11.3 gm (99%) of the title compound as a white, crystalline solid (m.p.=60–62° C.).

EA: Calculated for $C_9H_7BrO_2$: Theory: C, 47.61; H, 3.11. Found: C, 47.40; H, 3.37.

Preparation III 5-bromo-6-methoxybenzofuran

Beginning with 23 gm (113.3 mMol) 4-bromo-5-methoxyphenol, 16.2 gm of the title compound were prepared as a white crystalline solid essentially by the procedure of Preparation II.

Preparation IV 4-bromobenzofuran and 6-bromobenzofuran 2-(3-bromophenoxy)acetaldehyde Diethyl Acetal A solution of 10 gm (57.8 mMol) 3-bromophenol in 25 mL dimethylformamide was added dropwise to a mixture of 2.8 gm (70 mMol) sodium hydride (60% suspension in mineral oil) in 30 mL dimethylformamide. The reaction mixture was stirred for one hour after the addition was complete. To the reaction mixture was then added 9.7 mL (64.5 mMol) bromoacetaldehyde diethyl acetal and the resulting mixture was stirred at 153° C. for 2 hours. The reaction mixture was then allowed to cool to room temperature and was diluted with 300 mL diethyl ether. This mixture was then washed with two 150 ml portions of water, washed with 50 mL saturated aqueous sodium chloride, dried over magesium sulfate and concentrated under reduced pressure to provide about 17 gm of the desired compound.

$^1$H-NMR(CDCl$_3$): δ 7.15–7.05 (m, 2H), 6.85 (dd, 1H), 4.8 (t, 1H), 3.95 (d, 2H), 3.8–3.55 (m, 4H), 1.25 (t, 6H).

Cyclization

A mixture of 17 gm (57.8 mMol) 2-(3-bromophenoxy)acetaldehyde diethyl acetal and 17.5 gm polyphosphoric acid in 400 mL chlorobenzene was heated to 80° C. for 2 hours. The reaction mixture was cooled to room temperature and the chlorobenzene was decanted from the polyphosphoric acid. The polyphosphoric acid was washed with two 150 mL portions of diethyl ether. All or the organic phases were combined and concentrated under reduced pressure. The residue was redissolved in diethyl ether and the organic phases were washed with saturated aqueous sodium bicarbonate, water, and saturated aqueous sodium chloride, dried over magnesium sulfate and concentrated under reduced pressure. The residual oil was subjected to silica gel chromatography, eluting with hexane.

Fractions containing the faster eluting isomer were combined and concentrated under reduced pressure to provide 1.7 gm (15%) 4-bromobenzofuran.

EA: Calculated for $C_8H_5BrO$: Theory: C, 48.77; H, 2.56. Found: C, 48.89; H, 2.72.

Fractions containing the slower eluting isomer were combined and concentrated under reduced pressure to provide 2.5 gm (22%) 6-bromobenzofuran.

EA: Calculated for $C_8H_5BrO$: Theory: C, 48.77; H, 2.56. Found: C, 48.89; H, 2.67.

Preparation V 5-bromobenzofuran

Beginning with 10 gm (57.8 mMol) 4-bromophenol, 4.2 gm (38%) of the title compound were prepared essentially by the procedure described in Preparation IV.

EA: Calculated for $C_8H_5BrO$: Theory: C, 48.77; H, 2.56. Found: C, 48.51; H, 2.46.

Preparation VI 7-bromobenzofuran

Beginning with 10 gm (57.8 mMol) 2-bromophenol, 5 gm (45%) of the title compound were prepared essentially by the procedure described in Preparation IV.

EA: Calculated for $C_8H_5BrO$: Theory: C, 48.77; H, 2.56. Found: C, 49.02; H, 2.82.

Preparation VII 5-methoxy-7-bromobenzofuran 2-bromo-4-methoxyphenol

A solution of 2.6 mL (100 mmol) bromine in 10 mL carbon disulfide was added dropwise over 30 minutes to a solution of 12.4 gm (100 mMol) 4-methoxyphenol in 20 mL carbon disulfide at 0° C. After 30 minutes an additional 1 mL of bromine in 10 mL carbon disulfide are added dropwise. The reaction mixture was then concentrated under reduced pressure and the residue was dissolved in diethyl ether. This solution was washed sequentially with 100 mL water and 100 mL saturated aqueous sodium chloride, dried over magnesium sulfate and concentrated under reduced pressure. The residue was subjected to silica gel chromatography, eluting with a gradient of hexane containing from 0 to 20% ethyl acetate. Fractions containing product were combined and concentrated under reduced pressure to provide 11.6 gm (57%) of the desired compound as a crystalline solid.

$^1$H-NMR(CDCl$_3$): δ 7.0 (d, 1H), 6.95 (d, 1H), 6.8 (dd, 1H), 5.15 (s, 1H), 3.75 (s, 3H).

Beginning with 11.5 gm (56.9 mMol) 2-bromo-4-methoxyphenol, 4.5 gm (35%) of the title compound were prepared essentially by the procedure described in Preparation IV.

EA: Calculated for $C_9H_7BrO_2$: Theory: C, 47.61; H, 3.11. Found: C, 47.79; H, 3.13.

Preparation VIII 6-methoxy-7-bromobenzofuran 2-bromo-3-methoxyphenol

A solution of 22 gm (177.4 mMol) 3-methoxyphenol in 30 mL dihydropyran was added dropwise to a solution of 100 mg (0.525 mmol) p-toluenesulfonic acid monohydrate in 10 mL dihydropyran while cooling in an ice/water bath. After stirring for 1 hour the reaction mixture was diluted with 300 mL diethyl ether and then washed sequentially with 100 mL 0.1 N sodium hydroxide and 100 mL saturated aqueous sodium chloride. The remaining organic phase was dried over magnesium sulfate and concentrated under reduced pressure. The resulting oil was distilled. The fraction distilling at 110–130° C. was collected and then partitioned between 5 N sodium hydroxide and diethyl ether. The organic phase was separated, washed sequentially with water and saturated aqueous sodium chloride, dried over magnesium sulfate and concentrated under reduced pressure to provide 27.1 gm (73%) of tetrahydropyran-2-yl 3-methoxyphenyl ether.

$^1$H-NMR(CDCl$_3$): δ 7.18 (t, 1H), 6.65–6.60 (m, 2H), 6.50 (dd, 1H), 5.4 (t, 1H), 3.95–3.90 (m, 1H), 3.80 (s, 3H), 3.62–3.55 (m, 1H), 2.0–1.6 (m, 6H).

33 mL (52.8 mmol) n-butyllithium (1.6 M in hexane) were added dropwise to a solution 10 gm (48.1 mMol) tetrahydropyran-2-yl 3-methoxyphenyl ether in 100 mL tetrahydrofura over 15 minutes. After stirring for 2.5 hours at room temperature, the reaction mixture was cooled to 0° C. and then 4.6 mL (53.2 mMol) 1,2-dibromoethane were added dropwise. The reaction mixture was then allowed to stir at room temperature for about 14 hours. The reaction mixture was then diluted with 50 mL 1 N hydrochloric acid and was stirred for 1 hour. The aqueous phase was extracted with three 100 mL portions of diethyl ether. The organic phases were combined and extracted well with 5 N sodium hydroxide. These basic aqueous extracts were combined and cooled in an ice/water bath. The pH of this aqueous solution was adjusted to about 1 with 5 N hydrochloric acid and then extracted with three 100 mL portions of diethyl ether. These ether extracts were combined and washed with saturated aqueous sodium chloride, dried over magnesium sulfate and concentrated under reduced pressure. The resulting residue was subjected to silica gel chromatography, eluting with a gradient of hexane containing from 0 to 10% ethyl acetate. Fractions containing the desired compound were combined and concentrated under reduced pressure to provide 2.91 gm (30%) of a residue which crystallized upon standing.

EA: Calculated for C$_7$H$_7$BrO$_2$: Theory: C, 41.41; H, 3.48. Found: C, 41.81; H, 3.46.

Beginning with 6.9 gm (34 mmol) 2-bromo-3-methoxyphenol, 3.2 gm (41%) of the title compound were prepared as a white fluffy solid essentially by the procedure described in Preparation IV.

High Resolution MS: Calculated for C$_9$H$_7$BrO$_2$: Theory: 225.9629. Found: 225.9626.

Preparation IX 4-fluoro-7-bromobenzofuran

Beginning with 5 gm (26 mMol) 2-bromo-5-fluorophenol and 6.5 gm (39 mMol) bromoacetaldehyde ethylene glycol acetal, 3.3 gm (59%) of the title compound were prepared essentially by the procedure described in Preparation IV.

EA: Calculated for C$_8$H$_4$BrFO: Theory: C, 44.69; H, 1.88. Found: C, 44.44; H, 1.91.

Preparation X 5-bromo-7-fluorobenzofuran

Beginning with 20.5 gm (108 mMol) 2-fluoro-4-bromophenol, 3.0 gm (13%) of the title compound were prepared essentially by the procedure described in Preparation I.

$^1$H-NMR(CDCl$_3$): δ 7.65 (d, J=2.4 Hz, 1H), 7.50 (d, J=1.5 Hz, 1H), 7.19 (dd, J$_H$=1.5 Hz, J$_F$=8.3 Hz, 1H), 6.76 (m, 1H).

Preparation XI 6-fluoro-7-bromobenzofuran

Beginning with 7.5 gm (39.3 mMol) 2-bromo-3-fluorophenol, 10.83 gm (90%) 2-(2-bromo-3-fluorophenoxy)-acetaldehyde diethyl acetal was prepared essentially as described in Preparation IV.

Beginning with 5.0 gm (16.3 mMol) of 2-(2-bromo-3-fluorophenoxy)acetaldehyde diethyl acetal, 2.2 gm (63%) of the title compound were prepared essentially as described in Preparation IV.

Preparation XII 5-chloro-7-bromobenzofuran

Beginning with 25 gm (120.5 mmol) 2-bromo-4-chlorophenol, 41.16 gm crude 2-(2-bromo-4-chlorophenoxy)-acetaldehyde diethyl acetal was prepared essentially as described in Preparation IV. A sample of this crude material was subjected to silica gel chromatography to provide an analytical sample.

EA: Calculated for C$_{12}$H$_{16}$BrClO$_3$: Theory: C, 44.54; H, 4.98. Found: C, 44.75; H, 4.97.

Beginning with 20 gm (61.8 mMol) of 2-(2-bromo-4-chlorophenoxy)acetaldehyde diethyl acetal, 4.48 gm (31%) of the title compound were prepared as a crystalline solid essentially as described in Preparation I.

EA: Calculated for C$_8$H$_4$BrClO: Theory: C, 41.51; H, 1.74. Found: C, 41.67; H, 1.78.

Preparation XIII 4,5-difluoro-7-bromobenzofuran

Beginning with 5 gm (23.9 mMol) 2-bromo-4,5-difluorophenol, 7.05 gm (91%) 2-(2-bromo-4,5-difluorophenoxy)-acetaldehyde diethyl acetal were prepared essentially as described in Preparation IV.

EA: Calculated for C$_{12}$H$_{15}$BrF$_2$O$_3$: Theory: C, 44.33; H, 4.65. Found: C, 44.34; H, 4.41.

Beginning with 6.60 gm (20.3 mmol) of 2-(2-bromo-4,5-difluorophenoxy)acetaldehyde diethyl acetal, 0.42 gm (9%) of the title compound were prepared as a crystalline solid essentially as described in Preparation I.

EA: Calculated for C$_8$H$_3$BrF$_2$O: Theory: C, 41.24; H, 1.30. Found: C, 41.20; H, 1.51.

Preparation XIV 3-methyl-5-fluoro-7-bromobenzofuran 1-(2-bromo-4-fluorophenoxy)-2-propanone A mixture of 1.9 gm (10 mMol) 2-bromo-4-fluorophenol, 0.92 gm (10 mMol) chloroacetone, 0.1 gm potassium iodide, and 1.4 gm (10 mmol) potassium carbonate in 100 mL tetrahydrofuran was heated at reflux for 4 hours. The mixture was concentrated under reduced pressure and the residue partitioned between dichloromethane and 1 N sodium hydroxide. The phases were separated and the aqueous phase extracted well with dichloromethane. The organic phases were combined, washed with 1 N sodium hydroxide, dried over sodium sulfate and concentrated under reduced pressure. The residual was subjected to silica gel chromatography, eluting with hexane containing 20% ethyl acetate.

Fractions containing product were combined and concentrated under reduced pressure to provide 2.7 gm (100%) of the desired compound as a white solid.

Cyclization

Beginning with 2.7 gm (10 mmol) 1-(2-bromo-4-fluorophenoxy)-2-propanone and 15 gm polyphosphoric acid, 2.03 gm (81%) of the title compound were prepared as a yellow crystalline solid essentially as described in Preparation II.

Preparation XV 2-methyl-5-fluoro-7-bromobenzofuran

Ethyl 2-(2-bromo-4-fluorophenoxy)propionate

A mixture of 15 gm (78.5 mMol) 2-bromo-4-fluorophenol, 11.2 mL (86.4 mMol) ethyl 2-bromopropionate, and 13 gm (94.2 mMol) potassium carbonate was heated at reflux for 3 hours. At this point 0.1 gm potassium iodide were added and reflux continued for another 2 hours. The reaction mixture was partitioned between water and ethyl acetate. The phases were separated and the aqueous phase was extracted well with ethyl acetate. The organic phases were combined, washed with saturated aqueous sodium chloride, dried over sodium sulfate, and concentrated under reduced pressure. The residue was subjected to silica gel chromatography, eluting with hexane containing 5% ethyl acetate. Fractions containing product were combined and concentrated under reduced pressure to provide 19.8 gm (87%) of the desired compound as a clear oil.

2-(2-bromo-4-fluorophenoxy)propionaldehyde

A solution of 19.4 gm (66.7 mmol) ethyl 2-(2-bromo-4-fluorophenoxy)propionate in 400 mL toluene was cooled to −78° C. at which point 100 mL (100 mMol) diisobutylaluminum hydride (1 M in toluene) were added dropwise over 35 minutes. The reaction mixture was stirred at −78° C. for an additional 20 minutes after the addition was complete and then the reaction was quenched by the addition of methanol. The reaction mixture was warmed to room temperature and then treated with saturated aqueous sodium potassium carbonate. The mixture was stirred for 30 minutes and was then extracted well with ethyl acetate. The organic phases were combined, dried over sodium sulfate, and concentrated under reduced pressure to provide 16.9 gm of crude desired compound.

Cyclization

Beginning with 16.5 gm of the crude aldehyde, 5.2 gm (34% for the reduction and cyclization) of the title compound were prepared essentially as described in Preparation II.

Preparation XVI 5-nitro-7-bromobenzofuran

Potassium 5-nitro-7-bromobenzofuran-2-carboxylate

A mixture of 11.0 gm (44.7 mMol) 2-hydroxy-3-bromo-5-nitrobenzaldehyde, 5.56 gm (40.24 mmol) potassium carbonate, and 8.0 mL (46.95 mMol) diethyl bromomalonate in 55 mL 2-butanone was heated at reflux for 5 hours. The reaction mixture was cooled to room temperature and concentrated under reduced pressure. The residue was partitioned between 450 mL diethyl ether and 250 mL water and the aqueous phase was adjusted to pH of about 1 by the addition of dilute sulfuric acid. The phases were separated and the aqueous phase was extracted with two 150 mL portions of diethyl ether. The organic phases were combined, washed with 50 mL saturated aqueous sodium chloride, dried over magnesium sulfate and concentrated under reduced pressure. The residual solid was dissolved in 200 mL ethanol to which were added 4.8 gm (85.5 mMoL) potassium hydroxide. The resulting suspension was warmed on a steam bath for 1 hour. The suspension was then cooled to room temperature. After about 18 hours the mixture was filtered and dried under reduced pressure to provide 14.1 gm (98%) of the desired compound as an orange solid.

$^{13}$C-NMR(DMSO-d$_6$): δ 160.3, 159.8, 154.0, 143.9, 129.7, 122.2, 117.7, 108.0, 103.8.

5-nitro-7-bromobenzofuran-2-carboxylic Acid

A mixture of 11.5 gm (35.5 mMol) potassium 5-nitro-7-bromobenzofuran-2-carboxylate and 36 gm Dowex 50WX8-200 resin in 1.6 L methanol was stirred for 1 hour at room temperature. The mixture was filtered and the filtrate concentrated under reduced pressure. The residue was diluted with about 80 mL of methanol and heated on the steam bath with stirring. The mixture was cooled to room temperature and filtered. The residual solid was dried under vacuum to provide 6.7 gm (66%) of the desired compound as a gold solid.

m.p.=257° C. (dec.)

MS(FD): m/e=285, 287 (M$^+$)

EA: Calculated for C$_9$H$_4$NO$_5$Br: Theory: C, 37.79; H, 1.41; N, 4.90. Found: C, 37.81; H, 1.55; N, 4.77.

Decarboxylation

A sonicated mixture of 0.42 gm (1.47 mMol) 5-nitro-7-bromobenzofuran-2-carboxylic acid and 0.085 gm copper powder in 10 mL freshly distilled quinoline was heated at 185° C. under nitrogen for 7 minutes. The reaction mixture was cooled to room temperature and filtered. The solid recovered was washed with two 20 mL portions of dichloromethane and these washes were combined with the filtrate. The filtrate was then diluted with 70 mL dichloromethane and was washed sequentially with two 100 mL portions of 1 N hydrochloric acid, and 50 mL 4:1 saturated aqueous sodium chloride:5 N sodium hydroxide. The remaining organics were dried over sodium sulfate and concentrated under reduced pressure. The residue was subjected to silica gel chromatography, eluting with hexane containing 10% ethyl acetate. Fractions containing product were combined and concentrated under reduced pressure. The residual solid was crystallized from hexane to provide 0.15 gm (42%) of the title compound as fine, light orange needles.

m.p.=90–92° C.

MS(FD): m/e=241, 243 (M$^+$)

EA: Calculated for C$_8$H$_4$NO$_3$Br: Theory: C, 39.70; H, 1.67; N, 5.79. Found: C, 40.05; H, 2.03; N, 5.67.

Preparation XVII 3-trifluoromethyl-5-fluoro-7-bromobenzofuran

A solution of 2.10 gm (16.7 mmol) 1-trifluoromethyl-prop-1-en-3-ol, 3.19 gm (16.7 mMol) 2-bro and 4.81 gm (18.4 mMol) triphenylphosphine in 25 mL dichloromethane was cooled to 0° C. and then 2.9 mL (18.4 mMol) diethyl azodicarboxylate were added. The reaction mixture was stirred for 1 hour at room temperature and then the reaction mixture was directly subjected to flash silica gel chromatography, eluting with 20:1 hexane:ethyl acetate. Fractions containing product were combined and concentrated under reduced pressure to provide 6 gm of crude 1-(1-trifluoromethylprop-1-en-3-yloxy)-2-bromo-4-fluorobenzene.

1.0 gm (3.34 mMol) 1-(1-trifluoromethylprop-1-en-3-yloxy)-2-bromo-4-fluorobenzene was heated at 250° C. for 3 hours. The reaction mixture, containing primarily 2-(3-trifluoromethylprop-1-en-3-yl)-4-fluoro-6-bromophenol, was diluted with dichloromethane and the solution cooled to −78° C. This solution was then treated with excess ozone and was stirred at −78° C. until the 2-(3-trifluoromethylprop-1-en-3-yl)-4-fluoro-6-bromophenol was consumed as measured by thin layer chromatography. At this point the ozone was purged from the reaction with oxygen and then 0.88 gm (3.34 mMol) triphenylphosphine were added. The mixture was stored at −20° C. for about 64 hours. The reaction mixture was then concentrated under reduced pressure and the residue subjected to flash silica gel chromatography, eluting with hexane containing 10% ethyl acetate. Fractions containing the desired compound were combined and concentrated under reduced pressure to provide 2-hydroxy-3-trifluoromethyl-5-fluoro-7-bromo-2,3-dihydrobenzofuran. A solution of this dihydrobenzofuran in 10 mL toluene was treated with 4 drops of sulfuric acid and was stirred at reflux for 10 minutes. The reaction mixture was cooled to room temperature and was then washed with saturated aqueous sodium bicarbonate. The organic phase was separated and concentrated under reduced pressure. The residue was subjected to flash silica gel chromatography, eluting with hexane. Fractions containing product were combined and concentrated under reduced pressure to provide the title compound.

Preparation XVIII 5-methoxycarbonyl-7-bromobenzofuran

Beginning with methyl 3-bromo-4-allyloxybenzoate, the title compound was prepared essentially as described in Preparation XVII.

Preparation XIX 3-ethyl-5-fluoro-7-bromobenzofuran

Beginning with pent-2-en-1-yl 2-bromo-4-fluorophenyl ether, the title compound was prepared essentially as described in Preparation XVII.

Preparation XX 3-isopropyl-5-fluoro-7-bromobenzofuran

Beginning with 4-methylpent-2-en-1-yl 2-bromo-4-fluorophenyl ether, the title compound was prepared essentially as described in Preparation XVII.

Preparation XXI 3,4-dimethyl-5-fluoro-7-bromobenzofuran

Beginning with but-2-en-1-yl 2-bromo-4-fluoro-5-methylphenyl ether, the title compound was prepared essentially as described in Preparation XVII.

Preparation XXII 4-chloro-5-fluoro-7-bromobenzofuran

Bromination

A mixture of 5 gm (34.1 mMmol) 3-chloro-4-fluorophenol and 1.76 mL (34.1 mMol) bromine in 20 mL carbon disulfide was stirred at room temperature for 18 hours. The reaction mixture was concentrated under reduced pressure and the residue was dissolved in dichloromethane, washed with water, dried over sodium sulfate and concentrated under reduced pressure to provide a mixture of 2-bromo-4-fluoro-5-chlorophenol and 2-bromo-3-chloro-4-fluorophenol.

Ether Formation

This mixture of bromination isomers was combined with 12 gm allyl bromide and 13.6 gm potassium carbonate in 90 mL dimethylformamide. After stirring at room temperature for 2.5 hours, the mixture was partitioned between dichloromethane and water. The organic phases were combined, dried over sodium sulfate and concentrated under reduced pressure to provide 9.7 gm of a mixture of allyl ether isomers.

Rearrangement/Ozonolysis/Dehydration

The mixture of allyl ethers was reacted as described in Preparation XVII to provide 0.49 gm of the title compound as a white crystalline solid.

m.p.=84–85° C.

$^1$H-NMR(300 MHz, CDCl$_3$): δ 7.73 (d, J=2.1 Hz, 1H); 7.29 (d, J=8.8 Hz, 1H); 6.92 (d, J=2.1 Hz, 1H).

Preparation XXIII 4-trifluoromethyl-7-bromobenzofuran and 6-trifluoromethyl-7-bromobenzofuran 4-Trifluoromethylphenol was brominated essentially as described in Preparation XXII to provide a 58:12:30 mixture of 2-bromo-5-trifluoromethylphenol:2-bromo-3-trifluoromethylphenol: 4-bromo-3-trifluoromethylphenol. The 4-bromo-3-trifluoromethylphenol was separated from the other two isomers by silica gel chromatography. The remaining mixture of isomers was then alkylated to provide a mixture of 2-bromo-5-trifluorophenyl allyl ether and 2-bromo-3-trifluoromethylphenylallyl ether which was then separated by chromatography.

The 2-bromo-5-trifluoromethylphenyl allyl ether was converted to 4-trifluoromethyl-7-bromobenzofuran essentially as described in Preparation XXII.

$^1$H-NMR(300 MHz, CDCl$_3$): δ 7.81 (d, J=2.0 Hz, 1H); 7.55 (d, J=8.3 Hz, 1H); 7.41 (d, J=8.3 Hz, 1H); 7.03 (m, 1H).

The 2-bromo-3-trifluoromethylphenyl allyl ether was converted to 6-trifluoromethyl-7-bromobenzofuran essentially as described in Preparation XXII.

$^1$H-NMR(300 MHz, CDCl$_3$): δ 7.83 (d, J=1.9 Hz, 1H); 7.61 (d, J=8.3 Hz, 1H); 7.57 (d, J=8.3 Hz, 1H); 6.91 (d, J=1.9 Hz, 1H).

Preparation XXIV 5-trifluoromethyl-7-bromobenzofuran

Beginning with 5-trifluoromethylphenol, the title compound was prepared as described in Preparation XXII.

Preparation XXV

4,5,6-trifluoro-7-bromobenzofuran

Beginning with 3,4,5-trifluorophenol, the title compound was prepared essentially as described in Preparation XXII.

Preparation XXVI

4,6-dimethyl-5-chloro-7-bromobenzofuran

Beginning with 3,5-dimethyl-4-chlorophenol, the title compound was prepared essentially as described in Preparation XXII.

Preparation XXVII

Alternate Synthesis of 4,5-difluoro-7-bromobenzofuran 2-bromo-4,5-difluorophenyl Allyl Ether A mixture of 79.4 gm (0.38 mole) 2-bromo-4,5-difluorophenol and 79 gm (0.57 mole) potassium carbonate in 200 mL dimethylformamide was stirred at room temperature for 30 minutes. At this point 33 mL (0.38 mMol) allyl bromide were added and the resulting mixture was stirred for 18 hours at room temperature. The reaction mixture was then diluted with diethyl ether and washed with water followed by saturated aqueous sodium chloride. The remaining organics were dried over magnesium sulfate and concentrated under reduced pressure to provide 90 gm (96%) of the desired compound.

2-allyl-3,4-difluoro-6-bromophenol 15 gm (60.5 mmol) 2-bromo-4,5 difluorophenyl allyl ether was heated at 200° C. for 2 hours under a nitrogen atmosphere. The reaction mixture was cooled to room temperature and filtered through a pad of celite. The celite pad was washed with 500 mL hexane and the filtrate concentrated under reduced pressure. The residue was subjected to flash silica gel chromatography, eluting with hexane. Fractions containing product were combined and concentrated under reduced pressure to provide 9.7 gm (65%) of the desired compound.

(2-hydroxy-3-bromo-5,6-difluorophenyl)acetaldehyde

A solution of 7.8 gm (31.45 mMol) 2-allyl-3,4-difluoro-6-bromophenol in 100 mL dichloromethane and 20 mL methanol was cooled to −78° C. and was then saturated with ozone. After 20 minutes the reaction mixture was purged with nitrogen for 10 minutes and was then treated with 5 mL dimethylsulfide. The reaction mixture was allowed to warm gradually to room temperature. After 15 hours the reaction mixture was concentrated under reduced pressure to provide the title compound.

Cyclization

A mixture of 7.5 gm Amberlyst 15™ resin in 150 mL chlorobenzene was heated at 160° C. and the solvent distilled to remove water. The reaction mixture was cooled to 120° C. and then a solution of 31.45 mMol (2-hydroxy-3-bromo-5,6-difluorophenyl)acetaldehyde in chlorobenzene was added dropwise. The temperature was again increased to 160° C. and solvent distilled. After 1.5 hours, the reaction mixture was filtered and the filtrate concentrated under reduced pressure. The residue was subjected to silica gel chromatography, eluting with hexane. Fractions containing product were combined and concentrated under reduced pressure to provide 3.9 gm (53%) of the title compound as a white solid.

m.p.=46.5–48° C.

Preparation XXVIII

5-hydroxymethyl-7-bromobenzofuran

A solution of 0.63 gm (2.46 mmol) 5-methoxycarbonyl-7-bromobenzofuran in 10 mL toluene was cooled to −78° C. When material precipitated, 5 mL dichloromethane were added to effect solution. To this solution were then slowly added 1.5 mL (8.6 mmol) diisobutylaluminum hydride and the reaction mixture was allowed to warm gradually to room temperature. After 10 minutes the reaction was quenched by the addition of methanol followed by 1.5 gm sodium fluoride and 50 mL water and then Rochelle's salt solution. The mixture was diluted with additional dichloromethane and was stirred vigorously for about 1 hour. The phases were separated and the aqueous phase extracted well with ethyl acetate. The organic phases were combined and concentrated under reduced pressure. The residue was crystallized from hexane and dichloromethane to provide 0.46 gm (82%) of the title compound as a white crystalline solid.

Preparation XXIX

5-methoxymethyl-7-bromobenzofuran

A solution of 0.372 gm (0.40 mMol) 5-hydroxymethyl-7-bromobenzofuran in tetrahydrofuran was added to a mixture of 1.80 mmol sodium hydride (60% suspension in mineral oil) in 2 mL tetrahydrofuran. After stirring at room temperature for 1 hour, 204 µL iodomethane were added and stirring was continued for 2.5 hours. The reaction mixture was quenched by the addition of water and the resulting mixture was extracted well with ethyl acetate. The organic phase was concentrated under reduced pressure to provide a nearly quantitative yield of the title compound.

Preparation XXX

5-carboxy-7-bromobenzofuran

A solution of 0.52 gm (2.03 mMol) 5-methoxycarbonyl-7-bromobenzofuran and 0.41 gm (10.13 mMol) sodium hydroxide in 4 mL ethanol was stirred at room temperature until all of the starting material had been consumed. The reaction mixture was concentrated under reduced pressure and the residue dissolved in water. This solution was then made basic by the addition of 1N sodium hydroxide and was extracted well with ethyl acetate. The remaining aqueous phase was made acidic (pH about 2) by treatment with potassium hydrogen sulfate and the resulting solid removed by filtration. The aqueous phase was extracted well with ethyl acetate and the organics were combined and concentrated under reduced pressure to provide 0.40 gm (82%) of 5-carboxy-7-bromobenzofuran as an off-white solid.

MS(FD): m/e=240 (M−1)

Preparation XXXI

4-bromo-5-fluoro-, and 5-fluoro-6-bromobenzofuran

O-acetyl 3-bromo-4-fluorophenol

A solution of 1.09 gm (5 mMol) 3-bromo-4-fluoroacetophenone and 3.45 gm (20 mMol) m-chloroperbenzoic acid (70%) in 15 mL dichloromethane was heated at reflux for 18 hours. An additional 3.45 gm m-chloroperbenzoic acid were added and reflux continued for about 12 hours. At this point an additional 1.4 gm m-chloroperbenzoic acid were added and reflux continued for 18 hours. The reaction mixture was cooled to room temperature and was then diluted with 50 mL diethyl ether. The resulting mixture was cooled to 0° C. and was then treated with 15 mL 20% aqueous sodium thiosulfate. The resulting slurry was stirred for about 1 hour and then the phases separated. The organic phase was washed sequentially with 3×20 mL 20% aqueous sodium thiosulfate followed by 3×20 mL saturated aqueous sodium chloride. The organic phase was then dried over sodium sulfate and concentrated under reduced pressure. The residue was subjected to silica gel chromatography, eluting with 10:1 hexane:diethyl ether. Fractions containing product were combined and concentrated under reduced pressure to provide 68% of the desired compound.

3-bromo-4-fluorophenol

A solution of 0.80 gm (3.43 mMol) O-acetyl 3-bromo-4-fluorophenol in 10 mL 6% diisopropylethylamine in methanol was stirred at room temperature for 8 hours. The reaction mixture was concentrated under reduced pressure at 0° C. to provide the desired compound.

3-bromo-4-fluorophenyl Allyl Ether

A mixture of 0.65 gm (3.43 mMol) 3-bromo-4-fluorophenol, 0.60 mL (6.86 mMol) allyl bromide, and 0.71 gm (5.15 mMol) potassium carbonate in 6 mL acetone was stirred at reflux for 13 hours. The reaction mixture was concentrated under reduced pressure and the residue subjected to silica gel chromatography, eluting with hexane. Fractions containing product were combined and concentrated under reduced pressure to provide 61% of the desired compound.

Claisen Rearrangement 3-bromo-4-fluorophenyl allyl ether was placed in a sealed tube and was deoxygenated by bubbling nitrogen through the liquid. The tube was sealed and then heated at 230° C. for 3 hours. After cooling to room temperature, the mixture is subjected to silica gel chromatography, eluting with 8:1 hexane:diethyl ether. The faster eluting product isomer was 2-allyl-4-fluoro-5-bromophenol. The slower eluting isomer was 2-allyl-3-bromo-4-fluorophenol. The isomers were isolated in a ratio of 3:2 respectively.

4-bromo-5-fluorobenzofuran

Beginning with 3 gm (13 mMol) 2-allyl-3-bromo-4-fluorophenol, the title compound was prepared in 98% yield essentially by the procedure described in Preparation XXVII with the exception that the cyclization/dehydration step was performed using sulfuric acid in toluene.

5-fluoro-6-bromobenzofuran

Beginning with 3.5 gm (15 mMol) 2-allyl-4-fluoro-5-bromophenol, the title compound was prepared in 90% yield essentially by the procedure described in Preparation XXXI with the exception that the cyclization/dehydration step was performed using sulfuric acid in toluene.

Preparation XXXII

Alternate Synthesis of 4-chloro-5-fluoro-7-bromobenzofuran

A mixture of 90.4 gm (0.40 mole) 2-bromo-4-fluoro-5-chlorophenol (containing 10% 2-bromo-3-chloro-4-fluorophenol) and 64 gm (0.45 mole) hexamethylenetetramine was cooled in an ice bath. To this cooled mixture were added 306 mL trifluoroacetic acid. After stirring at about 0° C. for 15 minutes, the reaction mixture was heated at reflux for 1.5 hours. The reaction mixture was then cooled in an ice bath and treated with 439 mL of water followed by 220 mL 50% sulfuric acid. The reaction mixture was stirred without cooling for two hours. The reaction mixture was then diluted with 500 mL water and the resulting solid collected by filtration. The solid was washed with water until the wash was neutral (pH about 7). The solid was dried under reduced pressure and was then subjected to silica gel chromatography, eluting with a gradient of hexane containing from 0–2% ethyl acetate. Fractions containing the desired compound were combined and concentrated under reduced pressure to provide 57 gm (62%) 2-hydroxy-3-bromo-5-fluoro-6-chlorobenzaldehyde.

A suspension of 49.2 gm (0.19 mole) 2-hydroxy-3-bromo-5-fluoro-6-chlorobenzaldehyde and 127 gm (0.29 mole) (bromomethyl)triphenylphosphonium bromide in 230 mL tetrahydrofuran was cooled to 0° C. under a nitrogen atmosphere. To this were added dropwise 330 mL (0.33 mole) potassium tert-butoxide (1M in tetrahydrofuran) over 3 hours. An additional 90 mL (0.09 mole) potassium tert-butoxide (1M in tetrahydrofuran) were then added to react remaining starting material. The reaction mixture was diluted with 700 mL of hexane and the resulting precipitate removed by filtration. The recovered solid was slurried in 300 mL hexane and filtered 4 times. The combined filtrates were washed with 2×500 mL water followed by 500 mL saturated aqueous sodium chloride. The remaining organics were dried over sodium sulfate and concentrated under reduced pressure to provide a residual solid. This solid was slurried and filtered with 4×300 mL diethyl ether to remove triphenylphosphine oxide. The filtrates were concentrated and the residue subjected to silica gel chromatography, eluting with hexane. Fractions containing product were combined and concentrated under reduced pressure to provide 40 gm (83%) of the title compound as a white solid.

Preparation XXXIII

2(S)-methyl-5(S)-methylpiperazine

To a suspension of 2.7 gm (19 mmol) cyclo(L-Alanine-L-Alanine) in 95 mL tetrahydrofuran were added 115 mL (115 mmol) borane(1 M in tetrahydrofuran) over 25 minutes. The reaction mixture was stirred for one hour at room temperature and then at reflux for three hours. The reaction mixture was then allowed to cool to room temperature. While cooling in an ice bath, the reaction mixture was treated with 100 mL 1M hydrochloric acid over 10 minutes. The resulting mixture was concentrated under reduced pressure and the residual oil dissolved in 30 mL methanol followed by 25 mL 2M hydrogen chloride in diethyl ether. After heating at 60° C. for 1 hour, the resulting suspension was concentrated under reduced pressure. The residue was suspended in diethyl ether and stirred at room temperature for 1 hour. The crystalline precipitate was filtered and dried under reduced pressure at room temperature for 15 hours to provide 3.28 gm (92%) 2(S)-methyl-5(S)-methylpiperazine dihydrochloride.

A portion (0.48 gm) of the dihydrochloride salt was loaded on an SCX ion exchange column (10 gm). The column was washed with 100 mL 1:1 dichloromethane: methanol. The title compound was eluted with 7:3 dichloromethane containing 2M ammonia:methanol. Fractions containing product were combined and concentrated under reduced pressure to provide 0.25 gm (73%) of the title compound.

Preparation XXXIV

1-benzyl-3,3-ethylidenepiperazine

N-benzyl-N-[N'-tert-butoxycarbonyl 1-amino-1-cyclopropanecarbonyl]glycine Ethyl Ester To a solution of 1.36 gm (6.8 mmol) N-tert-butoxycarbonyl 1-amino-1-cyclopropanecarboxylic acid, 1.26 mL (13.5 mMol) N-benzylglycine ethyl ester, and 2.35 mL (13.5 mMol) diisopropylethylamine in 36 mL chloroform were added 2.57 gm (6.8 mMol) o-(7-azabenzotriazol-1-yl)-N,N,N',N'-tetramethyluronium hexafluorophosphate. The resulting mixture was stirred at room temperature over night and was then diluted with 70 mL dichloromethane. The reaction mixture was washed sequentially with 2×50 mL 1M hydrochloric acid, 2×35 mL 2N sodium hydroxide, and 50 mL saturated aqueous sodium chloride. The remaining organics were dried over magnesium sulfate concentrated under reduced pressure. The residue was treated with 65 mL diethyl ether and the resulting slurry filtered to provide 2.08 gm (82%) of the desired dipeptide.

1-benzyl-2,5-dioxo-3,3-ethylidenepiperazine 200 mL ethanol was cooled in an ice bath and stirred mechanically as 8.0 gm (102 mMol) acetyl chloride were added over 5 minutes. The mixture was stirred for 30 minutes at 0–5° C. and then a slurry of 3.84 gm (10.2 mmol) of the dipeptide in 50 mL ethanol was added. The mixture was stirred at 0° C. for 30 minutes and then at room temperature overnight. The reaction mixture was concentrated under reduced pressure and the residue dissolved in dichloromethane. This solution was washed sequentially with 2×75 mL saturated aqueous sodium bicarbonate and 50 mL saturated aqueous sodium chloride. The remaining organics were dried over sodium sulfate and concentrated under reduced pressure. The residue was treated with 20 mL diethyl ether and the resulting slurry filtered and dried to provide 1.97 gm (83%) of the desired bislactam.

Reduction

To a slurry of 0.70 gm (3 mMol) of the bislactam in 6 mL tetrahydrofuran were added 12.2 mL (12.2 mmol) borane (1M in tetrahydrofuran) over 20 minutes at room temperature under a nitrogen atmosphere. The reaction mixture was stirred at 60° C. overnight. After cooling to room temperature, the reaction mixture was carefully treated with 2 mL methanol and then concentrated under reduced pressure. The residue was treated with 20 mL methanol and 10 mL 1M hydrogen chloride in diethyl ether at 60° C. for 45 minutes, and was then concentrated under reduced pressure. The residue was passed through a SCX ion exchange column (10 gm), eluting with 7:3 dichloromethane:2M ammonia in methanol. Fractions containing product were combined and concentrated under reduced pressure to provide 0.46 gm (74%) of the title compound.

Preparation XXXV

1-benzyl-3(S)-isopropylpiperazine

N-benzyl-N-[N'-tert-butoxycarbonyl-(S)-valinyl]glycine Ethyl Ester

A solution of 6.18 gm (28.5 mMol) (S)-N-tert-butoxycarbonylvaline, 3.85 gm (28.5 mMol) 1-hydroxybenzotriazole, and 4.95 mL (28.5 mMol) diisopropylethylamine in 100 mL dichloromethane was cooled to 0° C. To this solution was added a solution of 5.46 gm (28.5 mMol) 1-(3-dimethylaminopropyl)-3-ethylcarbodiimide hydrochloride in 75 mL dichloromethane over 10 minutes. The reaction mixture was stirred for 25 minutes and then a solution of 5.0 gm (25.9 mMol) N-benzyl glycine ethyl ester in 25 mL dichloromethane was added over 10 minutes. The reaction mixture was allowed to warm gradually to room temperature and was stirred over night. The reaction mixture was concentrated under reduced pressure and the residue subjected to silica gel chromatography, eluting with dichloromethane containing from 0–3% methanol. Fractions containing product were combined and concentrated under reduced pressure to provide 7.1 gm (70%) of the desired dipeptide.

N-benzyl-N-[(S)-valinyl]glycine Ethyl Ester

A mixture of 5.82 gm (14.8 mMol) N-benzyl-N-[N'-tert-butoxycarbonyl-(S)-valinyl] glycine ethyl ester in 20 mL 4N hydrogen chloride in dioxane was stirred at room temperature under a nitrogen atmosphere over night. The reaction mixture was concentrated under reduced pressure and the residue partitioned between dichloromethane and saturated aqueous sodium bicarbonate. The aqueous phase was extracted again with dichloromethane. The combined organic phases were dried over magnesium sulfate and concentrated under reduced pressure to provide 4.2 gm (97%) of the desired compound as a yellow oil.

1-benzyl-2,5-dioxo-3(S)-isopropylpiperazine

A solution of 4.2 gm (14.4 Mol) N-benzyl-N-[(S)-valinyl] glycine ethyl ester and 1.2 mL (0.98 mMol) pyridine in 85 mL toluene was heated at reflux for 3 hours. The reaction mixture was then concentrated under reduced pressure to provide 3.4 gm (96%) of the desired compound as an oily solid.

1-benzyl-3(S)-isopropylpiperazine

To 100 mL tetrahydrofuran cooled to 0° C. were added 9 mL (8.9 mMol) lithium aluminum hydride (1.0 M in tetrahydrofuran) dropwise. To this was added dropwise a solution of 1.0 gm (4.06 mmol) 1-benzyl-2,5-dioxo-3(S)-isopropylpiperazine in 50 mL dichloromethane over 30 minutes. The reaction mixture was then heated at reflux over night. The reaction mixture was then cooled to 0° C. and was stirred vigorously while being treated sequentially with 1 mL water, 1 mL 5N sodium hydroxide, 2 mL water, and 5 gm sodium sulfate. After stirring for 30 minutes the reaction mixture was filtered and the filter cake washed with dichloromethane. The filtrate was concentrated under reduced pressure and the yellow waxy solid residue was subjected to silica gel chromatography, eluting with dichloromethane containing 0–3% methanol. Fractions containing product were combined and concentrated under reduced pressure to provide 0.38 gm (42%) of the title compound.

Other substituted piperazines may be prepared essentially as described in Preparation XXXV by substituting an appropriate amino acid for valine.

Preparation XXXVI

2(S)-(benzyloxymethyl)piperazine

A solution of 0.30 gm (1.01 mMol) 1-benzyl-2(S)-(benzyloxymethyl)piperazine in 20 mL 1,2-dichloroethane was cooled to 0° C. To this solution were added 1.09 mL (10.1 mMol) 1-chloroethyl chloroformate and the resulting mixture was heated at 80° C. for 4 hours. The reaction mixture was then cooled again to 0° C. and an additional 2.18 mL (20.2 mMol) 1-chloroethyl chloroformate were added. The reaction mixture was heated at reflux overnight and was then concentrated under reduced pressure. The residue was dissolved in 40 mL methanol and heated at reflux for 2 hours. The mixture was concentrated under reduced pressure and the residue subjected to silica gel chromatography, eluting with dichloromethane containing 0–10% methanol and 0.1% ammonium hydroxide. Fractions containing the desired product were combined and concentrated under reduced pressure to provide 0.17 gm (81%) of the title compound.

Preparation XXXVII

2(S)-benzylpiperazine

A mixture of 0.32 gm (1.2 mMol) 1-benzyl-3(S)-benzylpiperazine and 0.06 gm 20% palladium(II) hydroxide on carbon in 50 mL methanol was hydrogenated at room temperature over night at an initial hydrogen pressure of 50 p.s.i. The reaction mixture was filtered, the solid washed with methanol, and the filtrate concentrated under reduced pressure to provide 0.10 gm (50%) of the title compound.

Preparation XXXVIII

1-benzyl-2(S)-methyl-5(R)-methylpiperazine

To a solution of 32.4 gm (171 mMol) N-tert-butoxycarbonyl D-alanine, 171 mMol N-benzyl L-alanine methyl ester, and 59.6 mL (342 mMol) diisopropylethylamine in 925 mL chloroform were added 65 gm (171 mMol) O-(7-azabenzotriazol-1-yl)-N,N,N',N'-tetramethyluronium hexafluorophosphate. The resulting mixture was stirred for about 66 hours at room temperature. The reaction mixture was then washed sequentially with 3×500 mL 1N hydrochloric acid, 2×500 mL 1N sodium hydroxide, and 100 mL saturated aqueous sodium chloride. The remaining organic phase was dried over magnesium sulfate and concentrated under reduced pressure. The residual yellow oil was subjected to silica gel chromatography, eluting with a gradient of diethyl ether containing from 50–20% hexane. Fractions containing product were combined and concentrated under reduced pressure to provide 16.4 gm (26%) of the corresponding dipeptide (9:1 mixture of R,S and R,R diastereomers).

A solution of this dipeptide mixture in 100 mL methanol was added to a solution prepared by adding 32 mL (450 mMol) acetyl chloride to 200 mL methanol at 0–5° C. The resulting mixture was stirred at room temperature for 2.5 hours and was then concentrated under reduced pressure to provide a white foam. The residue was dissolved in dichloromethane and was then washed with 150 mL saturated aqueous sodium bicarbonate followed by 100 mL saturated aqueous sodium chloride. The remaining organic phase was dried over sodium sulfate and concentrated under reduced pressure. The residue was subjected to silica gel chromatography, eluting with a gradient of ethyl acetate containing from 0–100% acetone). Fractions containing product were combined and concentrated under reduced pressure to provide 8.8 gm (84%) of the corresponding R,S-bislactam.

A solution of 7.0 gm (30.1 mmol) R,S-bislactam in 150 mL tetrahydrofuran was cooled to 0° C. To this solution was added dropwise 300 mL 1M borane in tetrahydrofuran. The reaction mixture was stirred at room temperature for 50 minutes and then an additional 300 mL tetrahydrofuran were added. This mixture was stirred at reflux for 5 hours and was then cooled to 0° C. This cooled solution was treated carefully with 150 mL methanol and was then stirred at 0° C. for 30 minutes and then at room temperature for 30 minutes. The mixture was again cooled to 0° C. and then 5 mL concentrated hydrochloric acid were added. After 20 minutes at room temperature, the reaction mixture was concentrated under reduced pressure. The residue was dissolved in 300 mL diethyl ether and this solution was washed sequentially with 5N aqueous sodium hydroxide and saturated aqueous sodium chloride. The ether layer was dried over sodium sulfate and concentrated under reduced pressure to provide 5.9 gm (96%) of the title compound.

Preparation XXXIX

1-(N-[(triphenyl)methyl]amino)-2-amino-2-methylpropane

A solution of 10 mL (95.4 mMol) 1,2-diamino-2-methylpropane and 20 mL (144 mMol) triethylamine in 300 mL dichloromethane was cooled to 0° C. To this solution was added a solution of 26 gm (93.3 mMol) (triphenyl)methyl chloride in 50 mL dichloromethane. The resulting mixture was stirred at room temperature for about 18 hours. The reaction mixture was washed with saturated aqueous sodium bicarbonate, dried over magnesium sulfate, and concentrated under reduced pressure. The residue was subjected to silica gel chromatography, eluting with ethyl acetate containing from 0–10% methanol. Fractions containing product were combined and concentrated under reduced pressure to provide 16.0 gm (52%) of the desired compound as a white solid.

General Procedure I

Coupling of a Piperazine or Homopiperazine to a Benzofuran

One equivalent of an appropriately substituted benzofuran is dissolved in anhydrous toluene under nitrogen. The solution is treated with 4 equivalents of piperazine, 1.4 equivalents of sodium tert-butoxide, 0.15 equivalents racemic 2,2'-bis(diphenylphosphino)-1,1'-binaphthyl (BINAP), and 0.05 equivalents tris(dibenzylideneacetone)dipalladium ($Pd_2(dba)_3$). The reaction is evacuated and purged with nitrogen, and then heated at about 100° C. for about 5 hours. The reaction is cooled to room temperature, poured into ether, and filtered through celite. The filtrate is concentrated under reduced pressure, and the residue subjected to silica gel chromatography, eluting with a step gradient of 3% methanol in dichloromethane, 10% methanol in dichloromethane, and then with 9:1:0.1 dichloromethane:methanol:ammonium hydroxide. Fractions containing the product are combined and concentrated under reduced pressure to provide the desired benzofurylpiperazine. The benofurylpiperazine is then optionally treated with a pharamceutically acceptable acid if desired. The compounds of EXAMPLES 1–8 were prepared essentially as described in this procedure.

EXAMPLE 1

1-(4,5-difluorobenzofur-7-yl)piperazine Fumarate

Beginning with 4,5-difluoro-7-bromobenzofuran and piperazine, the title compound was prepared as described.
EA: Calculated for $C_{12}H_{12}N_2OF_2$—$C_4H_4O_4$: C, 54.24; H, 4.55; N, 7.91. Found: C, 53.95; H, 4.37; N, 7.71.

EXAMPLE 2

1-(4,6-difluorobenzofur-7-yl)piperazine Hydrochloride

Beginning with 4,6-difluoro-7-bromobenzofuran and piperazine, the title compound was prepared as described.
MS: m/e=239(M+H)

EXAMPLE 3

1-(4-fluoro-5-chlorobenzofur-7-yl)piperazine fumarate

Beginning with 4-fluoro-5-chloro-7-bromobenzofuran and piperazine, the title compound was prepared as described.

EXAMPLE 4

1-(4-chloro-5-fluorobenzofur-7-yl)piperazine Hydrochloride

Beginning with 4-chloro-5-fluoro-7-bromobenzofuran and piperazine, the title compound was prepared as described.
MS: m/e=255, 257(M+H)

EXAMPLE 5

1-(5-fluorobenzofur-5-yl)piperazine Hydrochloride

Beginning with 5-fluoro-4-bromobenzofuran and piperazine, the title compound was prepared as described.
MS: m/e=221(M+H)

EXAMPLE 6

1-(5-fluorobenzofur-6-yl)piperazine Hydrochloride

Beginning with 5-fluoro-6-bromobenzofuran and piperazine, the title compound was prepared as described.
MS: m/e=221(M+H)

EXAMPLE 7

1-(5-fluorobenzofur-7-yl)-2,6-dimethylpiperazine Hydrochloride

Beginning with 7-bromobenzofuran and 2,6-dimethylpiperazine, the title compound was prepared as described.
MS: m/e 249(M+H)

EXAMPLE 8

1-(5-fluorobenzofur-7-yl)homopiperazine Hydrochloride

Beginning with 5-fluoro-7-bromobenzofuran and homopiperazine, the title compound was prepared as described.
EA: Calculated for $C_{13}H_{15}N_2OF$—HCl: C, 57.67; H, 5.96; N, 10.35. Found: C, 57.73; H, 5.94; N, 10.07.

General Procedure II

Coupling of a 1-tert-Butoxycarbonylpiperazine to a Benzofuran

One equivalent of an appropriately substituted benzofuran is dissolved in anhydrous toluene under nitrogen. The solution is treated with 1.2 equivalents of N-tert-butoxycarbonylpiperazine, 1.4 equivalents of sodium tert-butoxide, 0.1 equivalents tri(o-tolyl)phosphine, and 0.05 equivalents tris (dibenzylideneacetone)dipalladium ($Pd_2(dba)_3$). The reaction is evacuated and purged with nitrogen, and then heated at about 100° C. for about 5 hours. The reaction is cooled to room temperature and filtered through a celite pad. The pad is washed with dichloromethane and the filtrate washed with water. The organic phase is dried over magnesium sulfate, concentrated under reduced pressure, and the residue subjected to silica gel chromatography, eluting with 20% ethyl acetate in hexane. The residue from this chromatography is again subjected to silica gel chromatography, eluting with 10% ethyl acetate in hexane. Fractions containing the 1-tert-butoxycarbonyl-4-benzofurylpiperazine are combined and concentrated under reduced pressure.

The 1-tert-butoxycarbonyl moiety is removed by treatment with either hydrogen chloride in dioxane or neat trifluoroacetic acid. The resulting benofurylpiperazine is then optionally treated with a pharmaceutically acceptable acid if desired. The compounds of EXAMPLES 9–25 were prepared essentially as described in this procedure.

EXAMPLE 9

1-(3-phenylbenzofur-7-yl)piperazine Oxalate

Beginning with 3-phenyl-7-bromobenzofuran and 1-tert-butoxycarbonylpiperazine, the title compound was prepared as described.
MS: m/e=279(M+H)

EXAMPLE 10

1-(3-ethylbenzofur-7-yl)piperazine Oxalate

Beginning with 3-ethyl-7-bromobenzofuran and 1-tert-butoxycarbonylpiperazine, the title compound was prepared as described.
MS: m/e=249(M+H)

EXAMPLE 11

1-(4,6-dimethyl-5-chlorobenzofur-7-yl)piperazine Oxalate

Beginning with 4,6-dimethyl-5-chloro-7-bromobenzofuran and 1-tert-butoxycarbonylpiperazine, the title compound was prepared as described.
MS: m/e=265(M+H)

EXAMPLE 12

1-(4-methyl-5-fluorobenzofur-7-yl)piperazine Oxalate

Beginning with 4-methyl-5-fluoro-7-bromobenzofuran and 1-tert-butoxycarbonylpiperazine, the title compound was prepared as described.
MS: m/e=235(M+H)

EXAMPLE 13

1-(3-ethyl-4,6-dimethyl-5-chlorobenzofur-7-yl)piperazine Oxalate

Beginning with 3-ethyl-4,6-dimethyl-5-chloro-7-bromobenzofuran and 1-tert-butoxycarbonylpiperazine, the title compound was prepared as described.
MS: m/e=293(M+H)

EXAMPLE 14

1-(3-isopropyl-5-fluorobenzofur-7-yl)piperazine Oxalate

Beginning with 3-isopropyl-5-fluoro-7-bromobenzofuran and 1-tert-butoxycarbonylpiperazine, the title compound was prepared as described.
MS: m/e=263(M+H)

EXAMPLE 15

1-(3-pentyl-5-fluorobenzofur-7-yl)piperazine Oxalate

Beginning with 3-pentyl-5-fluoro-7-bromobenzofuran and 1-tert-butoxycarbonylpiperazine, the title compound was prepared as described.
MS: m/e=291(M+H)

EXAMPLE 16

1-(5,6-difluorobenzofur-7-yl)piperazine Oxalate

Beginning with 5,6-difluoro-7-bromobenzofuran and 1-tert-butoxycarbonylpiperazine, the title compound was prepared as described.
MS: m/e=240(M+H)

EXAMPLE 17

1-(5-methoxycarbonylbenzofur-7-yl)piperazine Hydrochloride

Beginning with 5-methoxycarbonyl-7-bromobenzofuran and 1-tert-butoxycarbonylpiperazine, the title compound was prepared as described.
MS: m/e=261(M+H)

EXAMPLE 18

1-(4,6-dichlorobenzofur-7-yl)piperazine Oxalate

Beginning with 4,6-dichloro-7-bromobenzofuran and 1-tert-butoxycarbonylpiperazine, the title compound was prepared as described.
MS: m/e=271(M+H)

EXAMPLE 19

1-(5-(methoxymethyl)benzofur-7-yl)piperazine Oxalate

Beginning with 5-(methoxymethyl)-7-bromobenzofuran and 1-tert-butoxycarbonylpiperazine, the title compound was prepared as described.
MS: m/e=247(M+H)

EXAMPLE 20

1-(4,5,6-trifluorobenzofur-7-yl)piperazine Oxalate

Beginning with 4,5,6-trifluoro-7-bromobenzofuran and 1-tert-butoxycarbonylpiperazine, the title compound was prepared as described.
MS: m/e=257(M+H)

EXAMPLE 21

1-(3-methyl-4,5,6-trifluorobenzofur-7-yl)piperazine Oxalate

Beginning with 3-methyl-4,5,6-trifluoro-7-bromobenzofuran and 1-tert-butoxycarbonylpiperazine, the title compound was prepared as described.
MS: m/e=271(M+H)

EXAMPLE 22

1-(3-trifluoromethyl-5-fluorobenzofur-7-yl)piperazine Oxalate

Beginning with 3-trifluoromethyl-5-fluoro-7-bromobenzofuran and 1-tert-butoxycarbonylpiperazine, the title compound was prepared as described.
MS: m/e=289(M+H)

EXAMPLE 23

1-(4-methyl-5-fluorobenzofur-7-yl)piperazine Oxalate

Beginning with 4-methyl-5-fluoro-7-bromobenzofuran and 1-tert-butoxycarbonylpiperazine, the title compound was prepared as described.
MS: m/e=235(M+H)

EXAMPLE 24

1-(5-fluoro-6-methylbenzofur-7-yl)piperazine Oxalate

Beginning with 5-fluoro-6-methyl-7-bromobenzofuran and 1-tert-butoxycarbonylpiperazine, the title compound was prepared as described.
MS: m/e=325(M+H)

EXAMPLE 25

1-(4-chloro-5-methoxycarbonylbenzofur-7-yl)piperazine Oxalate

Beginning with 4-chloro-5-methoxycarbonyl-7-bromobenzofuran and 1-tert-butoxycarbonylpiperazine, the title compound was prepared as described.
MS: m/e=295(M+H)

General Procedure III

Coupling of 2(S)-Methyl-5(S)-Methylpiperazine to a Benzofuran

One equivalent of an appropriately substituted benzofuran is dissolved in anhydrous toluene under nitrogen. The solution is treated with 1.4 equivalents of sodium tert-butoxide, 0.04 equivalents racemic 2,2'-bis(diphenylphosphino)-1,1'-binaphthyl (BINAP), and 0.02 equivalents tris(dibenzylideneacetone)dipalladium ($Pd_2(dba)_3$). To this solution is then added a concentrated solution of 3.5 equivalents of 2(S)-methyl-5-(S)-methylpiperazine in dichloromethane. The reaction is evacuated and purged with nitrogen, and then heated at about 100° C. for about 2.5h. The reaction is cooled to room temperature, poured into ether, and filtered through celite. The filtrate is concentrated under reduced pressure, and the residue subjected to silica gel chromatography eluting with 95:5 dichloromethane containing 2M ammonia:methanol. Fractions containing the product are combined and concentrated under reduced pressure to provide the desired benzofurylpiperazine. The benofurylpiperazine is then optionally treated with a pharmaceutically acceptable acid if desired. The compounds of EXAMPLES 26–28 were prepared essentially as described in this procedure.

EXAMPLE 26

1-(4-fluoro-5-chlorobenzofur-7-yl)-2(S)-methyl-5 (S)-methylpiperazine Fumarate Beginning with 4-fluoro-5-chloro-7-bromobenzofuran and 2(S)-methyl-5(S)-methylpiperazine, the title compound was prepared as described.

EA: Calculated for $C_{14}H_{16}N_2OClF$—$C_4H_4O_4$: C, 54.21; H, 5.05; N, 7.02. Found: C, 54.05; H, 5.08; N, 6.80.

EXAMPLE 27

1-(4-chloro-5-fluorobenzofur-7-yl)-2(S)-methyl-5 (S)-methylpiperazine Fumarate Beginning with 4-chloro-5-fluoro-7-bromobenzofuran and 2(S)-methyl-5(S)-methylpiperazine, the title compound was prepared as described.

EA: Calculated for $C_{14}H_{16}N_2OClF$—$C_4H_4O_4$: C, 54.21; H, 5.05; N, 7.02. Found: C, 54.50; H, 4.86; N, 6.80.

EXAMPLE 28

1-(5-fluorobenzofur-7-yl)-2(S)-methyl-5(S)-methylpiperazine Fumarate

Beginning with 5-fluoro-7-bromobenzofuran and 2(S)methyl-5(S)-methylpiperazine, the title compound was prepared as described.

EA: Calculated for $C_{14}H_{17}N_2OF$—$C_4H_4O_4$: C, 59.33; H, 5.81; N, 7.69. Found: C, 59.44; H, 5.91; N, 7.46.

General Procedure IV

Preparation of 1-(Benzofuryl)-3-Substituted-Piperazines

One equivalent of an appropriately substituted benzofuran is dissolved in anhydrous toluene under nitrogen. The solution is treated with 1.2 equivalents of a 2-substituted piperazine, 1.4 equivalents of sodium tert-butoxide, 0.04–0.15 equivalents racemic 2,2'-bis(diphenylphosphino)-1,1'-binaphthyl (BINAP), and 0.02–0.05 equivalents tris(dibenzylideneacetone)dipalladium ($Pd_2(dba)_3$). The reaction is evacuated and purged with nitrogen, and then heated at about 100° C. for about 5 hours. The reaction is cooled to room temperature and stirred for about 15 hours. The reaction mixture is then poured into ether and filtered through celite. The filtrate is concentrated under reduced pressure, and the residue subjected to silica gel chromatography, eluting with a step gradient of 3% methanol in dichloromethane, 6% methanol in dichloromethane, and 9:1:0.1 dichloromethane:methanol:—ammonium hydroxide. Fractions containing the product are combined and concentrated under reduced pressure to provide the desired benzofurylpiperazine. The benofurylpiperazine is then optionally treated with a pharmaceutically acceptable acid if desired. The compounds of EXAMPLES 29–48 were prepared essentially as described in this procedure.

EXAMPLE 29

1-(5-fluorobenzofur-7-yl)-3(S)-methylpiperazine Hydrochloride

Beginning with 5-fluoro-7-bromobenzofuran and 2(S)-methylpiperazine, the title compound was prepared as described.

EA: Calculated for $C_{13}H_{15}N_2OF$—HCl: C, 57.67; H, 5.96; N, 10.35. Found: C, 57.84; H, 5.81; N, 10.13.

$[\alpha]_D = -26.9°$ (c=1.03, methanol)

EXAMPLE 30

1-(7-fluorobenzofur-5-yl)-3(S)-methylpiperazine Hydrochloride

Beginning with 5-bromo-7-fluorobenzofuran and 2(S)-methylpiperazine, the title compound was prepared as described.

HRMS: Calculated for $C_{13}H_{15}N_2OF$: 235.1247. Found: 235.1243.

EXAMPLE 31

1-(5-fluorobenzofur-7-yl)-3(S)-benzyloxymethylpiperazine Fumarate

Beginning with 5-fluoro-7-bromobenzofuran and 2(S)-benzyloxymethylpiperazine, the title compound was prepared as described.

MS: m/e=341(M+H)

EXAMPLE 32

1-(4,5-difluorobenzofur-7-yl)-3(S)-methylpiperazine Fumarate

Beginning with 4,5-difluoro-7-bromobenzofuran and 2(S)-methylpiperazine, the title compound was prepared as described.

EA: Calculated for $C_{13}H_{14}N_2OF_2$—$C_4H_4O_4$: C, 55.44; H, 4.93; N, 7.61. Found: C, 55.48; H, 4.90; N, 7.51.

EXAMPLE 33

1-(5-fluorobenzofur-7-yl)-3(S)-isopropylpiperazine Fumarate

Beginning with 5-fluoro-7-bromobenzofuran and 2(S)isopropylpiperazine, the title compound was prepared as described.
MS: m/e 263(M+H)

EXAMPLE 34

1-(5-fluorobenzofur-7-yl)-3(S)-propylpiperazine Fumarate

Beginning with 5-fluoro-7-bromobenzofuran and 2(S)-propylpiperazine, the title compound was prepared as described.
EA: Calculated for $C_{15}H_{19}N_2OF$—$C_4H_4O_4$: C, 60.31; H, 6.13; N, 7.40. Found: C, 60.31; H, 6.00; N, 7.28.

EXAMPLE 35

1-(5-fluorobenzofur-7-yl)-3(S)-butylpiperazine Fumarate

Beginning with 5-fluoro-7-bromobenzofuran and 2(S)-butylpiperazine, the title compound was prepared as described.
MS: m/e=277(M+H)

EXAMPLE 36

1-(5-chlorobenzofur-7-yl)-3(S)-methylpiperazine Fumarate

Beginning with 5-chloro-7-bromobenzofuran and 2(S)-methylpiperazine, the title compound was prepared as described.
MS: m/e=251(M+H)

EXAMPLE 37

1-(5-fluorobenzofur-7-yl)-3(S)-benzylpiperazine Fumarate

Beginning with 5-fluoro-7-bromobenzofuran and 2(S)-benzylpiperazine, the title compound was prepared as described.
MS: m/e=311(M+H)

EXAMPLE 38

1-(5,6-difluorobenzofur-7-yl)-3(S)-methylpiperazine Oxalate

Beginning with 5,6-difluoro-7-bromobenzofuran and 2(S)-methylpiperazine, the title compound was prepared as described.
MS: m/e=253(M+H)

EXAMPLE 39

1-(4,5,6-trifluorobenzofur-7-yl)-3(S)-methylpiperazine Oxalate

Beginning with 4,5,6-trifluoro-7-bromobenzofuran and 2(S)-methylpiperazine, the title compound was prepared as described.
MS: m/e=271(M+H)

EXAMPLE 40

1-(3-methyl-4,5,6-trifluorobenzofur-7-yl)-3(S)-methylpiperazine Oxalate

Beginning with 3-methyl-4,5,6-trifluoro-7-bromobenzofuran and 2(S)-methylpiperazine, the title compound was prepared as described.
MS: m/e 285(M+H)

EXAMPLE 41

1-(4-chloro-5-fluorofluorobenzofur-7-yl)-3(S)-methylpiperazine Hydrochloride

Beginning with 4-chloro-5-fluoro-7-bromobenzofuran and 2(S)-methylpiperazine, the title compound was prepared as described.
MS: m/e=269, 271(M+H)

EXAMPLE 42

1-(5-fluorofluorobenzofur-7-yl)-3(S)-ethylpiperazine Fumarate

Beginning with 5-fluoro-7-bromobenzofuran and 2(S)-ethylpiperazine, the title compound was prepared as described.

EXAMPLE 43

1-(4-methyl-5-fluorofluorobenzofur-7-yl)-3(S)-methylpiperazine Hydrochloride

Beginning with 4-methyl-5-fluoro-7-bromobenzofuran and 2(S)-methylpiperazine, 1-(4-methyl-5-fluorofluorobenzofur-7-yl)-3(S)-methylpiperazine was prepared as described. A solution of this material in methanol was treated with a methanolic solution containing one equivalent of ammonium chloride. The mixture was slowly concentrated under reduced pressure. The residue was triturated with diethyl ether and the solid collected by filtration to provide the title compound.
High Resolution MS: Calculated for: 249.1403. Found: 249.1409.

EXAMPLE 44

1-(4-chloro-5-fluorobenzofur-7-yl)-3,3-ethylidenepiperazine Hydrochloride

Beginning with 4-chloro-5-fluoro-7-bromobenzofuran and 2,2-ethylidenepiperazine, the title compound was prepared as described.
MS: m/e=281, 283(M+H)

EXAMPLE 45

1-(4-trifluoromethylbenzofur-7-yl)-3,3-ethylidene-piperazine Hydrochloride

Beginning with 4-trifluoromethyl-7-bromobenzofuran and 2,2-ethylidenepiperazine, the title compound was prepared as described.

MS: m/e 297(M+H)

EXAMPLE 46

1-(5-fluorobenzofur-7-yl)-3(R)-methylpiperazine Hydrochloride

Beginning with 5-fluoro-7-bromobenzofuran and 2(R)-methylpiperazine, the title compound was prepared as described.

MS: m/e=235(M+H)

EXAMPLE 47

1-(7-fluorobenzofur-5-yl)-3(R)-methylpiperazine Hydrochloride

Beginning with 5-bromo-7-fluorobenzofuran and 2(R)-methylpiperazine, the title compound was prepared as described.

HRMS: Calculated for $C_{13}H_{15}N_2OF$: 235.1247. Found: 235.1236.

EXAMPLE 48

1-(5-fluorobenzofur-4-yl)-3(R)-methylpiperazine Hydrochloride

Beginning with 4-bromo-5-fluorobenzofuran and 2(R)-methylpiperazine, the title compound was prepared as described.

MS: m/e=235(M+H)

General Procedure V

Preparation of 1-(Benzofuryl)-2-Substituted-Piperazines

One equivalent of an appropriately substituted benzofuran is dissolved in anhydrous toluene under nitrogen. The solution is treated with 1.0–1.2 equivalents of a 1-benzyl-3-substituted piperazine, 1.4 equivalents of sodium tert-butoxide, 0.04 equivalents racemic 2,2'-bis(diphenylphosphino)-1,1'-binaphthyl (BINAP), and 0.02 equivalents tris(dibenzylideneacetone)dipalladium ($Pd_2(dba)_3$). The reaction is evacuated and purged with nitrogen, and then heated at about 100° C. for about 5 hours. The reaction is cooled to room temperature and stirred for about 15 hours. The reaction mixture is then poured into ether and filtered through celite. The filtrate is concentrated under reduced pressure, and the residue subjected to silica gel chromatography, eluting with a step gradient hexanes to 10% ethyl acetate in hexanes. Fractions containing the 4-benzyl-2-substituted-1-benzofurylpiperazine are combined and concentrated under reduced pressure.

The 4-benzyl-2-substituted-1-benzofurylpiperazine is dissolved in 1,2-dichloroethane and the resulting solution cooled in an ice bath as 2 equivalents 1-chloroethyl chloroformate are added dropwise. The reaction mixture is then heated at reflux for 1.5 hours and then concentrated under reduced pressure. The residue is dissolved in anhydrous methanol and the solution heated at reflux for 1.5 hours. This mixture is concentrated under reduced pressure and the residue partitioned between dichloromethane and saturated aqueous sodium bicarbonate. The aqueous phase is extracted well with dichloromethane. The combined organic phases are dried over magnesium sulfate and concentrated under reduced pressure.

Preferably the residue from the evaporation of methanol supra is treated with diethyl ether and the solid isolated by filtration. This solid may be converted to the free base as previously described. Alternatively, the methanol solution may be subjected to ion exchange chromatography to provide the free base.

The residual oil from any of these procedures is subjected to flash silica gel chromatography, eluting with a gradient of dichloromethane, 6% methanol in dichloromethane, and 9:1:0.1 dichlormethane:methanol:ammonium hydroxide. Fractions containing the 1-benzofuryl-2-substituted piperazine are then combined and concentrated under reduced pressure.

The 1-benzofuryl-2-substituted-piperazine is then optionally treated with a pharmaceutically acceptable acid if desired. The compounds of EXAMPLES 49–68 were prepared essentially as described in this procedure.

EXAMPLE 49

1-(5-fluorobenzofur-7-yl)-2(S)-methylpiperazine Hydrochloride

Beginning with 5-fluoro-7-bromobenzofuran and 1-benzyl-3(S)-methylpiperazine, the title compound was prepared as described.

EA: Calculated for $C_{13}H_{15}N_2OF$—HCl: C, 57.67; H, 5.96; N, 10.35. Found: C, 57.94; H, 6.08; N, 10.44.

EXAMPLE 50

1-(5-fluorobenzofur-7-yl)-2(S)-methylpiperazine Fumarate

Beginning with 5-fluoro-7-bromobenzofuran and 1-benzyl-3(S)-methylpiperazine, the title compound was prepared as described.

EA: Calculated for $C_{13}H_{15}N_2OF$—$C_4H_4O_4$: C, 58.28; H, 5.47; N, 8.00. Found: C, 58.14; H, 5.40; N, 7.94.

EXAMPLE 51

1-(5-chlorobenzofur-7-yl)-2(S)-methylpiperazine Hydrochloride

Beginning with 5-chloro-7-bromobenzofuran and 1-benzyl-3(S)-methylpiperazine, the title compound was prepared as described.

MS: m/e=251(M+H)

HRMS: Calculated for $C_{13}H_{15}N_2OCl$: Theory: 251.0951. Found: 251.0934.

EXAMPLE 52

1-(5-chlorobenzofur-7-yl)-2(S)-methylpiperazine Fumarate

Beginning with 5-chloro-7-bromobenzofuran and 1-benzyl-3(S)-methylpiperazine, the title compound was prepared as described.
EA: Calculated for $C_{13}H_{15}N_2OCl$—$C_4H_4O_4$: C, 55.67; H, 5.22; N, 7.64. Found: C, 55.45; H, 4.96; N, 7.36.

EXAMPLE 53

1-(7-fluorobenzofur-5-yl)-2(S)-methylpiperazine Fumarate

Beginning with 5-bromo-7-fluorobenzofuran and 1-benzyl-3(S)-methylpiperazine, the title compound was prepared as described.
HRMS: Calculated for $C_{13}H_{15}N_2OF$: 235.1247. Found: 235.1240.

EXAMPLE 54

1-(5-fluorobenzofur-7-yl)-2(S)-(benzyloxymethyl)piperazine Fumarate

Beginning with 5-fluoro-7-bromobenzofuran and 1-benzyl-3(S)-(benzyloxymethyl)piperazine, the title compound was prepared as described.
MS: m/e=341(M+H)
HRMS: Calculated for $C_{20}H_{21}N_2O_2F$: Theory: 341.1665. Found: 341.1669.

EXAMPLE 55

1-(5-fluorobenzofur-7-yl)-2(S)-propylpiperazine Hydrochloride

Beginning with 5-fluoro-7-bromobenzofuran and 1-benzyl-3(S)-propylpiperazine, the title compound was prepared as described.
MS: m/e 263(M+H)

EXAMPLE 56

1-(5-fluorobenzofur-7-yl)-2(S)-benzylpiperazine Fumarate

Beginning with 5-fluoro-7-bromobenzofuran and 1-benzyl-3(S)-benzylpiperazine, the title compound was prepared as described.
HRMS: Calculated for $C_{19}H_{19}N_2OF$: 311.1560. Found: 311.1558.

EXAMPLE 57

1-(4,5-difluorobenzofur-7-yl)-2(S)-methylpiperazine Fumarate

Beginning with 4,5-difluoro-7-bromobenzofuran and 1-benzyl-3(S)-methylpiperazine, the title compound was prepared as described.
EA: Calculated for $C_{13}H_{15}N_2OCl$—$C_4H_4O_4$: C, 55.44; H, 4.93; N, 7.61. Found: C, 55.40; H, 4.97; N, 7.40.

EXAMPLE 58

1-(5-methoxybenzofur-7-yl)-2(S)-methylpiperazine Fumarate

Beginning with 5-methoxy-7-bromobenzofuran and 1-benzyl-3(S)-methylpiperazine, the title compound was prepared as described.

EXAMPLE 59

1-(5-fluorobenzofur-7-yl)-2(S)-(sec-butyl)piperazine Fumarate

Beginning with 5-fluoro-7-bromobenzofuran and 1-benzyl-3(S)-(sec-butylpiperazine, the title compound was prepared as described.
HRMS: Calculated for $C_{16}H_{21}N_2OF$: 277.1716. Found: 277.1714.

EXAMPLE 60

1-(5-fluorobenzofur-7-yl)-2(S)-isopropylpiperazine Fumarate

Beginning with 5-fluoro-7-bromobenzofuran and 1-benzyl-3(S)-isopropylpiperazine, the title compound was prepared as described.
MS: m/e=263(M+H)

EXAMPLE 61

1-(5-trifluoromethylbenzofur-7-yl)-2(S)-methylpiperazine Fumarate

Beginning with 5-trifluoromethyl-7-bromobenzofuran and 1-benzyl-3(S)-methylpiperazine, the title compound was prepared as described.
MS: m/e=285(M+H)

EXAMPLE 62

1-(4-trifluoromethylbenzofur-7-yl)-2(S)-methylpiperazine Fumarate

Beginning with 4-trifluoromethyl-7-bromobenzofuran and 1-benzyl-3(S)-methylpiperazine, the title compound was prepared as described.
MS: m/e=285 (M+H)

EXAMPLE 63

1-(5-fluorobenzofur-7-yl)-2(R)-methylpiperazine Hydrochloride

Beginning with 5-fluoro-7-bromobenzofuran and 1-benzyl-3(R)-methylpiperazine, the title compound was prepared as described.

EXAMPLE 64

1-(7-fluorobenzofur-5-yl)-2(R)-methylpiperazine Fumarate

Beginning with 5-bromo-7-fluorobenzofuran and 1-benzyl-3(R)-methylpiperazine, the title compound was prepared as described.
HRMS: Calculated for $C_{13}H_{15}N_2OF$: 235.1247. Found: 235.1252.

EXAMPLE 65

1-(5-chlorobenzofur-7-yl)-2(R)-methylpiperazine Fumarate

Beginning with 5-chloro-7-bromobenzofuran and 1-benzyl-3(R)-methylpiperazine, the title compound was prepared as described.

EXAMPLE 66

1-(5-trifluoromethylbenzofur-7-yl)-2(R)-methylpiperazine Fumarate

Beginning with 5-trifluoromethyl-7-bromobenzofuran and 1-benzyl-3(R)-methylpiperazine, the title compound was prepared as described.
MS: m/e=285(M+H)

EXAMPLE 67

1-(5-fluorobenzofur-7-yl)-2,2-ethylidenepiperazine Fumarate

Beginning with 5-fluoro-7-bromobenzofuran and 1-benzyl-3,3-ethylidenepiperazine, the title compound was prepared as described.
HRMS: Calculated for $C_{14}H_{15}N_2OF$: 247.1247. Found: 247.1248.

EXAMPLE 68

1-(5-fluorobenzofur-7-yl)-2(S)-ethylpiperazine Hydrochloride

Beginning with 5-fluoro-7-bromobenzofuran and 1-benzyl-3(S)-ethylpiperazine, the title compound was prepared as described.

EXAMPLE 69 trans-1-(4,6-difluorobenzofur-7-yl)-2,5-dimethylpiperazine Hydrochloride

Beginning with 0.58 gm (2.5 mMol) 4,6-difluoro-7-bromobenzofuran and 1.23 gm (10.80 mMol) trans-2,5-dimethylpiperazine, trans-1-(4,6-difluorobenzofur-7-yl)-2,5-dimethylpiperazine was prepared in 51% yield essentially as described in GENERAL PROCEDURE III. Treatment of this compound with hydrogen chloride provided the title compound.
MS: m/e=267(M+H)

EXAMPLE 70 cis-1-(5-fluorobenzofur-7-yl)-2,3-dimethylpiperazine Hydrochloride

Beginning with 1.53 gm (7.12 mMol) 5-fluoro-7-bromobenzofuran and 3.2 gm (28.5 mMol) cis-2,3-dimethylpiperazine, cis-1-(5-fluorobenzofur-7-yl)-2,3-dimethylpiperazine was prepared in 30% yield essentially as described in GENERAL PROCEDURE III. Treatment of this compound with hydrogen chloride provided the title compound.
MS: m/e=249(M+H)

EXAMPLE 71

1-(6-fluorobenzofur-7-yl)piperazine Hydrochloride

Beginning with 0.11 gm (0.52 mMol) 6-fluoro-7-bromobenzofuran and 0.096 gm (0.52 mmol) 1-tert-butoxycarbonylpiperazine, 0.085 gm (64%) of the title compound were prepared essentially as described in GENERAL PROCEDURE II.
MS: m/e=233(M+H)

EXAMPLE 72

1-(5-methyl-6-fluorobenzofur-7-yl)piperazine Hydrochloride

Beginning with 0.25 gm (1.11 mMol) 5-methyl-6-fluoro-7-bromobenzofuran and 0.22 gm (1.16 mMol) 1-tert-butoxycarbonylpiperazine, the title compound was prepared essentially as described in GENERAL PROCEDURE II.

EXAMPLE 73

1-(5-fluoro-6-chlorobenzofur-7-yl)piperazine Hydrochloride

Beginning with 0.26 gm (1.06 mMol) 5-fluoro-6-chloro-7-bromobenzofuran and 0.22 gm (1.16 mMol) 1-tert-butoxycarbonylpiperazine, the title compound was prepared essentially as described in GENERAL PROCEDURE II.
MS: m/e=257 (M+1)

EXAMPLE 74

1-(5-(hydroxymethyl)benzofur-7-yl)piperazine Hydrochloride 5-(hydroxymethyl)-7-bromobenzofuran
A solution of 1.1 gm (4.31 mMol) 5-(methoxycarbonyl)-7-bromobenzofuran in 20 ml dichloromethane was cooled to −78° C. To this solution were then added 2.7 ml (15.1 mMol) diisobutylaluminum hydride. The reaction mixture was allowed to warm to room temperature and was then stirred for 10 minutes. To the reaction mixture were then added 2.5 gm sodium fluoride and 815 μL water. The resulting mixture was diluted with an additional 10 ml dichloromethane and was then stirred for about 1 hour. The suspension was filtered and the filtrate concentrated under reduced pressure to provide 0.50 gm (51%) of the desired compound. The recovered solid was partitioned between 200 ml ethyl acetate and 100 ml Rochelle's Salt solution for 2 hours. This mixture was filtered, the phases separated, and the organic phase concentrated under reduced pressure to provide an additional 0.30 gm (31%) of the desired compound.
MS: m/e=228(M+H)

5-(tert-butyldimethylsilyloxymethyl)-7-bromobenzofuran
A mixture of 0.40 gm (1.76 mMol) 5-(hydroxymethyl)-7-bromobenzofuran, 0.24 gm (30.5 mMol) imidazole, and 0.26 gm (1.76 mMol) tert-butyldimethylsilyl chloride in 2 ml dimethylformamide was stirred at room temperature overnight. The reaction mixture was then partitioned between hexane and water. The organic phase was washed with well with water, dried over magnesium sulfate and concentrated under reduced pressure to provide 0.51 gm (85%) of the desired compound.
Ion Spray MS: m/e=228 (M-(tert-butyldimethylsilyl))

1-(5-(tert-butyldimethylsilyloxymethyl)benzofur-7-yl)-4-tert-butoxycarbonylpiperazine Beginning with 0.51 gm (1.5 mMol) 5-(tert-butyldimethylsilyloxymethyl)-7-bromobenzofuran and 0.30 gm (1.6 mMol) 1-tert-butoxycarbonylpiperazine, 0.42 gm (63%) of the desired compound were prepared essentially as described in GENERAL PROCEDURE II.

Deprotection

A mixture of 0.42 gm 1-(5-(tert-butyldimethylsilyloxymethyl)benzofur-7-yl)-4-tert-butoxycarbonylpiperazine and excess tetrabutylammonium fluoride was stirred in tetrahydrofuran for 30 minutes. The reaction mixture was then diluted with ethyl acetate and washed three times with dilute aqueous sodium bicarbonate. The remaining organics were dried over magnesium sulfate and concentrated under reduced pressure. The residue was subjected to silica gel chromatography, eluting with 5:2 hexane:ethyl acetate. Fractions containing product were combined and concentrated under reduced pressure to provide 0.28 gm (89%) 1-(5-(hydroxymethyl)benzofur-7-yl)-4-tert-butoxycarbonylpiperazine. This material was dissolved in trifluoroacetic acid and the resulting solution stirred at room temperature for 2 hours. The reaction mixture was concentrated under reduced pressure and the residue subjected to silica gel chromatography, eluting with dichloromethane containing 10% methanol and a trace of ammonia. Fractions containing product were combined and concentrated under reduced pressure to provide 1-(5-hydroxymethyl)benzofur-7-yl)piperazine. This compound was treated with hydrogen chloride to provide the title compound as a white solid.

MS: m/e=233(M+H)

EXAMPLE 75

1-(4,6-difluorobenzofur-7-yl)-3(S)-methylpiperazine Hydrochloride

Beginning with 0.58 gm (2.5 mmol) 4,6-difluoro-7-bromobenzofuran and 0.14 gm (0.73 mmol) 2(S)-methylpiperazine, the title compound was prepared essentially as described in GENERAL PROCEDURE IV.

MS: m/e=253(M+H)

EXAMPLE 76

1-(4,5,6-trifluorobenzofur-7-yl)-3(S)-methylpiperazine Hydrochloride

Beginning with 0.13 gm (0.51 mMol) 4,5,6-trifluoro-7-bromobenzofuran and 0.064 gm (0.51 mmol) 2(S)-methylpiperazine, the title compound was prepared essentially as described in GENERAL PROCEDURE IV.

MS: m/e=271(M+H)

EXAMPLE 77

1-(6-fluorobenzofur-7-yl)-3(S)-methylpiperazine Hydrochloride

Beginning with 1.0 gm (4.6 mMol) 6-fluoro-7-bromobenzofuran and 0.49 gm (4.9 mMol) 2(S)-methylpiperazine, the title compound was prepared essentially as described in GENERAL PROCEDURE IV.

MS: m/e=235(M+H)

EXAMPLE 78

1-(5-fluoro-6-chlorobenzofur-7-yl)-3(S)-methylpiperazine Hydrochloride

Beginning with 0.27 gm (1.11 mMol) 5-fluoro-6-chloro-7-bromobenzofuran and 0.11 gm (1.11 mMol) 2(S)-methylpiperazine, the title compound was prepared essentially as described in GENERAL PROCEDURE IV.

MS: m/e=269 (M+1)

EXAMPLE 79

1-(5-fluorobenzofur-4-yl)-3(S)-methylpiperazine Hydrochloride

Beginning with 0.72 gm (3.33 mMol) 4-bromo-5-fluorobenzofuran and 1.33 gm (13.3 mMol) 2(S)-methylpiperazine, the title compound was prepared essentially as described in GENERAL PROCEDURE IV.

MS: m/e=235(M+H)

EXAMPLE 80

1-(4,6-difluorobenzofur-7-yl)-3(R)-methylpiperazine Hydrochloride

Beginning with 0.58 gm (2.5 mMol) 4,6-difluoro-7-bromobenzofuran and 1.08 gm (10.8 mMol) 2(R)-methylpiperazine, the title compound was prepared essentially as described in GENERAL PROCEDURE IV.

MS: m/e=253(M+H)

EXAMPLE 81

1-(5-methyl-6-fluorobenzofur-7-yl)-3(R)-methylpiperazine Hydrochloride

Beginning with 0.31 gm (1.35 mMol) 5-methyl-6-fluoro-7-bromobenzofuran and 0.14 gm (1.35 mMol) 2(R)-methylpiperazine, the title compound was prepared essentially as described in GENERAL PROCEDURE IV.

EXAMPLE 82

1-(6-fluorobenzofur-7-yl)-3(R)-methylpiperazine Hydrochloride

Beginning with 0.14 gm (0.67 mMol) 6-fluoro-7-bromobenzofuran and 0.068 gm (0.67 mMol) 2(R)-methylpiperazine, the title compound was prepared essentially as described in GENERAL PROCEDURE IV.

MS: m/e=235(M+H)

EXAMPLE 83

1-(4,6-dichlorobenzofur-7-yl)-3(R)-methylpiperazine Hydrochloride

Beginning with 0.31 gm (1.2 mmol) 4,6-dichloro-7-bromobenzofuran and 0.12 gm (1.2 mMol) 2(R)-methylpiperazine, the title compound was prepared essentially as described in GENERAL PROCEDURE IV.

MS: m/e=286(M+H)

EXAMPLE 84

1-(5-fluoro-6-chlorobenzofur-7-yl)-3(R)-methylpiperazine Hydrochloride

Beginning with 0.24 gm (0.95 mmol) 5-fluoro-6-chloro-7-bromobenzofuran and 0.09 gm (0.95 mmol) 2(R)-methylpiperazine, the title compound was prepared essentially as described in GENERAL PROCEDURE IV.

MS: m/e=269 (M+1)

EXAMPLE 85

N-[butyl] 7-(piperazin-1-yl)benzofuran-5-carboxamide Dihydrochloride

To a solution of 0.055 gm (0.16 mmol) 7-(4-tert-butoxycarbonylpiperazin-1-yl)benzofuran-5-carboxylic aci 0.5 ml dichloromethane were added sequentially 0.034 gm (0.18 mMol) 1-(3-dimethylaminopropyl)-3-ethylcarbodiimide hydrochloride, 20 μL (0.19 mMol) butylamine and a catalytic amount of dimethylaminopyridine. The mixture was agitated over night at room temperature and was then diluted with ethyl acetate. This solution was washed sequentially with 1N sodium hydroxide and water. The remaining organics were concentrated under reduced pressure and the residue subjected to silica gel chromatography, eluting with dichloromethane containing 2% 2N methanolic ammonia. Fractions containing N-[butyl] 7-(1-tert-butoxycarbonylpiperazin-1-yl)benzofuran-5-carboxamide were combined and concentrated under reduced pressure. The residue was dissolved in trifluoroacetic acid and stirred at room temperature for about 2 hours. The volatiles were removed under reduced pressure and the residue treated with hydrogen chloride to provide the title compound.

MS: m/e=302(M$^+$)

EXAMPLE 86

N-[2-(pyridin-3-yl)ethy-1-yl] 7-(piperazin-1-yl)benzofuran-5-carboxamide Dihydrochloride Beginning with 0.046 gm (0.13 mMol) 7-(4-tert-butoxycarbonylpiperazin-1-yl)benzofuran-5-carboxylic acid and 19 μL (0.17 mMol)-3-(2-aminoethyl)pyridine, 0.042 gm (75%) of the title compound were prepared essentially as described in EXAMPLE 101.

MS: m/e=351(M+H)

EXAMPLE 87

N-[2-(pyridin-2-yl)ethy-1-yl] 7-(piperazin-1-yl)benzofuran-5-carboxamide Dihydrochloride Beginning with 0.050 gm (0.14 mMol) 7-(4-tert-butoxycarbonylpiperazin-1-yl)benzofuran-5-carboxylic acid and 21 μL (0.17 mMol) 2-(2-aminoethyl)pyridine, 0.036 gm (59%) of the title compound were prepared essentially as described in EXAMPLE 101.

MS: m/e=351(M+H)

EXAMPLE 88

1-(4-chloro-5-fluorobenzofur-7-yl)-2(R)-methylpiperazine Fumarate

Beginning with 4-chloro-5-fluoro-7-bromobenzofuran and 1-benzyl-3 (R)-methylpiperazine, the title compound was prepared essentially as described in GENERAL PROCEDURE V.

EA: Calculated for $C_{13}H_{14}N_2OClF—C_4H_4O_4$: C, 53.06; H, 4.72; N, 7.28. Found: C, 52.84; H, 4.57; N, 7.21.

General Procedure VI

Coupling of Benzofurans with 1-(Benzyl)-2,5-Disubstituted-Piperazines

One equivalent of an appropriately substituted benzofuran is dissolved in anhydrous toluene under nitrogen. The solution is treated with 1.0–1.2 equivalents of a 1-benzyl-2,5-disubstituted piperazine, 1.4 equivalents of sodium tert-butoxide, 0.04 equivalents racemic 2,2'-bis(diphenylphosphino)-1,1'-binaphthyl (BINAP), and 0.02 equivalents tris(dibenzylideneacetone)dipalladium (Pd$_2$(dba)$_3$). The reaction is evacuated and purged with nitrogen, and then heated at about 100° C. for about 5 hours. The reaction is cooled to room temperature and stirred for about 15 hours. The reaction mixture is then poured into ether and filtered through celite. The filtrate is concentrated under reduced pressure, and the residue subjected to ion exchange chromatography (Varian SCX 60 cc/10 gm), eluting sequentially with dichloromethane containing 50% methanol, methanol, and then 2M ammonia in ethanol. Fractions containing the 4-benzyl-2,5-disubstituted-1-benzofurylpiperazine are combined and concentrated under reduced pressure.

The 4-benzyl-2,5-disubstituted-1-benzofurylpiperazine is then debenzylated and the salt formed essentially as described in GENERAL PROCEDURE V. The compounds of EXAMPLES 89–93 were prepared essentially as described in this procedure.

EXAMPLE 89

1-(5-fluorobenzofur-7-yl)-2(R)-methyl-5(S)-methylpiperazine Fumarate

Beginning with 5-fluoro-7-bromobenzofuran and 1-benzyl-2(S)-methyl-5(R)-methylpiperazine, the title compound was prepared essentially as described.

m.p.=179–182° C.

EA: Calculated for $C_{14}H_{17}N_2OF—C_4H_4O_4$: C, 59.33; H, 5.81; N, 7.69. Found: C, 59.05; H, 5.78; N, 7.44.

EXAMPLE 90

1-(4-chloro-5-fluorobenzofur-7-yl)-2(R)-methyl-5(S)-methylpiperazine Fumarate

Beginning with 4-chloro-5-fluoro-7-bromobenzofuran and 1-benzyl-2(S)-methyl-5(R)-methylpiperazine, the title compound was prepared essentially as described.

HRMS: Calculated for $C_{14}H_{16}N_2OClF$: Theory: 283.1013. Found: 283.1017.

EXAMPLE 91

1-(4-methyl-5-fluorobenzofur-7-yl)-2(R)-methyl-5(S)-methylpiperazine Fumarate

Beginning with 4-methyl-5-fluoro-7-bromobenzofuran and 1-benzyl-2(S)-methyl-5(R)-methylpiperazine, the title compound was prepared essentially as described.

EA: Calculated for $C_{15}H_{19}N_2OF$—$C_4H_4O_4$: C, 60.31; H, 6.13; N, 7.40. Found: C, 60.57; H, 5.84; N, 7.28.

EXAMPLE 92

1-(5-chlorobenzofur-7-yl)-2(R)-methyl-5(S)-methylpiperazine Fumarate

Beginning with 5-chloro-7-bromobenzofuran and 1-benzyl-2(S)-methyl-5(R)-methylpiperazine, the title compound was prepared essentially as described.

EXAMPLE 93

1-(5-fluorobenzofur-7-yl)-2(R)-methyl-5(R)-methylpiperazine Fumarate

Beginning with 5-fluoro-7-bromobenzofuran and 1-benzyl-2(R)-methyl-5(R)-methylpiperazine, the title compound was prepared essentially as described.

HRMS: Calculated for $C_{14}H_{17}N_2OF$: Theory: 249.1403. Found: 249.1394.

EXAMPLE 94

1-(5-fluorobenzofur-7-yl)-2,2-dimethylpiperazine Fumarate 1-(triphenylmethyl)amino-2-(5-fluorobenzofur-7-yl)amino-2-methylpropane A mixture of 5.0 gm (23.3 mmol) 5-fluoro-7-bromobenzofuran, 10.3 gm (32.6 mmol) 1-(triphenylmethyl)amino-2-amino-2-methylpropane, 0.87 gm (1.4 mMol) racemic 2,2'-bis(diphenylphosphino)-1,1'-binaphthyl, 0.64 gm (0.7 mMol) tris(dibenzylideneacetone)dipalladium, and 3.13 gm (32.5 mMol) sodium tert-butoxide in 60 ml anhydrous toluene was degassed and purged with nitrogen. The reaction mixture was heated at reflux for 2 hours and was then allowed to cool to room temperature. The reaction mixture was diluted with 50 mL diethyl ether, filtered through celite, and the filtrate concentrated under reduced pressure. The residue was subjected to silica gel chromatography, eluting with 15:1 hexane:ethyl acetate. Fractions containing product were combined and concentrated under reduced pressure to provide 7.6 gm (70%) of the desired product.

1-(5-fluorobenzofur-7-yl)-2,2-dimethyl-5,6-dioxopiperazine

A solution of 7.6 gm (16.4 mmol) 1-(triphenylmethyl)-amino-2-(5-fluorobenzofur-7-yl)-amino-2-methylpropane in 300 mL dichloromethane was cooled to 0° C. To this solution were added 10.1 mL (72.3 mmol) triethylamine followed by 3 mL (32.7 mMol) methyl chlorooxoacetate. The mixture was stirred at room temperature for 18 hours and then additional charges of 10.1 mL (72.3 Mmol) triethylamine and 3 mL (32.7 mMol) methyl chlorooxoacetate were added. After stirring for 4 hours, the reaction mixture was washed with saturated aqueous sodium bicarbonate, dried over magnesium sulfate, and concentrated under reduced pressure. The residue was subjected to silica gel chromatography, eluting with hexane containing 50% ethyl acetate. Fractions containing product were combined and concentrated under reduced pressure to provide 3.2 gm (70%) of the desired compound.

Reduction

To a suspension of 0.55 gm (2 mMol) 1-(5-fluorobenzofur-7-yl)-2,2-dimethyl-5,6-dioxopiperazine in 20 mL tetrahydrofuran were added 5 mL (10 mMol) borane dimethylsulfide complex (2M in tetrahydrofuran). After stirring at room temperature for about 18 hours, the reaction mixture was quenched by the dropwise addition of methanol. When gas evolution upon methanol addition had ceased to occur, 1.5 mL concentrated hydrochloric acid were added and the resulting mixture stirred for 15 minutes. The reaction mixture was concentrated under reduced pressure and the residue subjected to ion exchange chromatography (Varian SCX 60 cc/10 gm), eluting sequentially with methanol and then 1:1 dichloromethane:2M ammonia in methanol. Fractions containing product were combined and concentrated under reduced pressure. The residue was dissolved in dichloromethane and treated with di-tert-butyl dicarbonate. After stirring for 2 hours at room temperature, the reaction mixture was concentrated under reduced pressure. The residue was subjected to silica gel chromatography, eluting with hexane containing 20% ethyl acetate. Fractions containing product were combined and concentrated under reduced pressure to provide 0.59 gm (85%) 1-(5-fluorobenzofur-7-yl)-2,2-dimethyl-4-(tert-butoxycarbonyl)piperazine. This material was dissolved in 10 mL 4M hydrogen chloride in dioxane, and was stirred at room temperature for 3 hours. The reaction mixture was concentrated under reduced and the residue subjected to ion exchange chromatography (Varian SCX 60 cc/10 gm), eluting sequentially with methanol and then 1:1 dichlormethane:2M ammonia in methanol. Fractions containing product were combined and concentrated under reduced pressure to provide 1-(5-fluorobenzofur-7-yl)-2,2-dimethylpiperazine. This material was treated with fumaric acid to provide 0.40 gm (68%) of the title compound.

m.p.=162–165° C.

HRMS: Calculated for $C_{14}H_{17}N_2OF$: Theory: 249.1403. Found: 249.1400.

EXAMPLE 95

1-(5,6-difluorobenzofur-7-yl)piperazine Hydrochloride

Beginning with 0.31 gm (1.33 mMol) 5,6-difluoro-7-bromobenzofuran and 0.27 gm (1.46 mmol) 1-(tert-butoxycarbonyl)piperazine, the title compound was prepared essentially as described in GENERAL PROCEDURE II.

EXAMPLE 96

1-(3,4-dimethyl-5-fluorobenzofur-7-yl)piperazine Oxalate

Beginning with 0.22 gm (0.93 mMol) 3,4-dimethyl-5-fluoro-7-bromobenzofuran and 0.19 gm (1.02 mmol) 1-(tert-butoxycarbonyl)piperazine, the title compound was prepared essentially as described in GENERAL PROCEDURE II.

MS(ES): m/e=249 (M+1)

EXAMPLE 97

1-(5-cyano-6-fluorobenzofur-7-yl)piperazine Hydrochloride

Beginning with 5-cyano-6-fluoro-7-bromobenzofuran and 1-(tert-butoxycarbonyl)piperazine, the title compound was prepared essentially as described in GENERAL PROCEDURE II.

MS(ES): m/e=246 (M+1)

EXAMPLE 98 cis- and trans-1-(5-fluorobenzofur-6-yl)piperazine Hydrochloride

Coupling 0.26 gm (1.21 mmol) 5-fluoro-6-bromobenzofuran with 0.55 gm (4.84 mmol) 2,5-dimethylpiperazine under the conditions described in GENERAL PROCEDURE III provided two components.

The trans-isomer was the faster eluting isomer, and was converted to the hydrochloride salt.

MS(ES): m/e=249 (M$^+$)

The cis-isomer was the slower eluting isomer, and was also converted to the hydrochloride salt.

MS(ES): m/e=249 (M$^+$)

EXAMPLE 99

1-(4-fluorobenzofur-7-yl)-3(R)-methylpiperazine Oxalate

Beginning with 4-fluoro-7-bromobenzofuran and 2(R)-methylpiperazine, the title compound was prepared essentially as described in GENERAL PROCEDURE IV.

m.p.=192° C. (dec.)

MS(FD): m/e=235 (M+1)

EA: Calculated for $C_{13}H_{15}N_2OF$—$C_2H_2O_4$: C, 55.55; H, 5.28; N, 8.64. Found: C, 55.48; H, 5.15; N, 8.64.

EXAMPLE 100

1-(4-fluorobenzofur-7-yl)-3(S)-methylpiperazine Oxalate

Beginning with 4-fluoro-7-bromobenzofuran and 2(S)-methylpiperazine, the title compound was prepared essentially as described in GENERAL PROCEDURE IV.

m.p.=191° C. (dec.)

MS(FD): m/e=235 (M+1)

EA: Calculated for $C_{13}H_{15}N_2OF$—$C_2H_2O_4$: C, 55.55; H, 5.28; N, 8.64. Found: C, 55.40; H, 5.37; N, 8.53.

EXAMPLE 101

1-(5,6-difluorobenzofur-7-yl)-3(R)-methylpiperazine Hydrochloride

Beginning with 5,6-difluoro-7-bromobenzofuran and 2(R)-methylpiperazine, the title compound was prepared essentially as described in GENERAL PROCEDURE IV.

MS(ES): m/e=253 (M$^+$)

EXAMPLE 102

1-(5,6-difluorobenzofur-7-yl)-3(S)-methylpiperazine Hydrochloride

Beginning with 5,6-difluoro-7-bromobenzofuran and 2(S)-methylpiperazine, the title compound was prepared essentially as described in GENERAL PROCEDURE IV.

MS(ES): m/e=253 (M$^+$)

EXAMPLE 103

1-(5-methyl-6-fluorobenzofur-7-yl)-3(S)-methylpiperazine Hydrochloride

Beginning with 5-methyl-6-fluoro-7-bromobenzofuran and 2(S)-methylpiperazine, the title compound was prepared essentially as described in GENERAL PROCEDURE IV.

MS(ES): m/e=248 (M$^+$)

EXAMPLE 104

1-(3-methyl-6-fluorobenzofur-7-yl)-3(R)-methylpiperazine Hydrochloride

Beginning with 3-methyl-6-fluoro-7-bromobenzofuran and 2(R)-methylpiperazine, the title compound was prepared essentially as described in GENERAL PROCEDURE IV.

MS(ES): m/e=248 (M$^+$)

EXAMPLE 105

1-(3-methyl-6-fluorobenzofur-7-yl)-3(S)-methylpiperazine Hydrochloride

Beginning with 3-methyl-6-fluoro-7-bromobenzofuran and 2(R)-methylpiperazine, the title compound was prepared essentially as described in GENERAL PROCEDURE IV.

MS(ES): m/e=248 (M$^+$)

EXAMPLE 106

1-(6-fluorobenzofur-7-yl)-2(S)-methylpiperazine Hydrochloride

Beginning with 6-fluoro-7-bromobenzofuran and 1-benzyl-3(S)-methylpiperazine, the title compound was prepared essentially as described in GENERAL PROCEDURE V.

MS(ES): m/e=235 (M+1)

EXAMPLE 107

1-(4,5,6-trifluorobenzofur-7-yl)-2(S)-methylpiperazine Hydrochloride

Beginning with 4,5,6-trifluoro-7-bromobenzofuran and 1-benzyl-3(S)-methylpiperazine, the title compound was prepared essentially as described in GENERAL PROCEDURE V.

MS(ES): m/e=270 (M$^+$)

EXAMPLE 108

Isolation of Diastereomers of cis-1-(5-fluorobenzofur-7-yl)2,3-dimethylpiperazine A diastereomeric mixture of cis-1-(5-fluorobenzofur-7-yl)-2,3-dimethylpiperazine (EXAMPLE 85) was subjected to chiral chromatography on a 4.6×250 mm ChiralPak AD column, eluting with heptane containing 2% ethanol and 0.2% dimethylethylamine. A faster and slower eluting diastereomer was recovered substantially free of the other diastereomer.

The ability of the compounds of this invention to bind to the 5-HT$_{2c}$ receptor subtype was measure essentially as described by Wainscott (Wainscott, et al., *Journal of Pharmacology and Experimental Therapeutics*, 276, 720–727 (1996)).

Membrane Preparation

AV12 cells stably transfected with the human 5-HT$_{2c}$ receptors were grown in suspension and harvested by centrifugation, resuspended in 50 mM tris-HCl, pH 7.4, and frozen at −70° C. On the day of assay, an aliquot of cells was thawed, resuspended in 40 mL of 50 mM tris-HCl, pH 7.4, and centrifuged at 39,800×g for 10 minutes at 4° C. The resulting pellet was resuspended, incubated at 37° C. for 10 minutes to remove endogenous serotonin, then centrifuged twice more.

[$^{125}$I]-DOI Binding for Determination of 5-HT$_{2c}$ Receptor Affinity

Briefly, prepared cell membranes were added to dilutions of compounds in a final solution containing 50 mM tris-HCl, pH 7.4, 9.75 mM MgCl$_2$, 0.5 mM EDTA, 10 µM pargyline, 0.1% sodium ascorbate, and 0.1 nM [$^{125}$I]-DOI, with 10 µM mianserin for defining non-specific binding. All incubations (800 µL) were performed at 37° C. for 30 minutes before harvesting onto GF/C filters prewet with 0.5% polyethyleneimine, with four 1 mL washes of ice-cold 50 mM tris-HCl, pH 7.4, and counting in a gamma counter. Non-linear regression analysis was performed on the concentration response curves using a four parameter logistic equation described by DeLean (DeLean, et al., *Molecular Pharmacology*, 21, 5–16 (1982)). IC$_{50}$ values were converted to K$_i$ values using the Cheng-Prusoff equation (Cheng, et al., *Biochem. Pharmacol.*, 22, 3099–3108 (1973)).

Representative compounds of the present invention were found to have affinity for the 5-HT$_{2c}$ receptor as measured essentially by the procedure described supra.

The 5-HT$_{2c}$ receptor is functionally coupled to specific G-proteins. Agonist activation of 5-HT$_{2c}$ G-protein-coupled receptors results in the release of GDP from the •-subunit (G alpha q or G alpha i) of the G-protein and the subsequent binding of GTP. The binding of the stable analog [$^{35}$S]-GTPγS is an indicator of this receptor's activation.

[$^{35}$S]-GTPγS Binding

The immunoadsorption scintillation proximity assay (ISPA) in microtiter plates of [$^{35}$S]-GTPγS binding to G alpha q or G alpha i was modified from published conditions (DeLapp et al, JPET 289 (1999) 946–955). Test compounds were dissolved in DMSO and diluted in assay buffer consisting of 50 mM Tris-HCl (pH 7.4), 10 mM MgCl$_2$, 100 mM NaCl, and 0.2 mM EGTA. Incubations were performed over 12 test concentrations; volume was 200 µl. The incubation also contained 0.1 µM GDP and 0.25 nM [$^{35}$S]-GTPγS. Membrane homogenates from AV12 cells stably transfected with the human 5-HT$_{2c}$ receptor were added and the microtiter plates were incubated for 30 minutes at room temperature. The incubation was terminated by the addition of Nonidet P-40 (final concentration of 0.27%), followed by addition of rabbit polyclonal anti-G alpha q/11 antibody (0.2 µg per well), and anti-rabbit scintillation proximity assay beads (Amersham; 1.25 mg per well; final volume was 290 µl). The mixture was incubated for 3 hours at room temperature to complete the immunoadsorption of [$^{35}$S]-GTPγS bound to G alpha q/11. Microtiter plates were centrifuged briefly to pellet beads. [$^{35}$S]-GTPγS binding was quantitated by microtiter plate scintillation spectrometry (Wallac). Data analysis was performed by nonlinear regression analysis with GraphPad Prism software running on a personal computer, using 5-HT control concentration-response curves to define maximal stimulation of [$^{35}$S]-GTPγS binding.

Representative compounds of the present invention were tested in the [$^{35}$S]-GTPγS assay and were found to be agonists of the 5-HT$_{2c}$ receptor.

The ability of agonists of the 5-HT$_{2c}$ receptor in general, and the compounds of the present invention in particular, to treat obesity is demonstrated by testing in a feeding assay.

Fasted Feeding Assay

Male rats were fasted for 18 hours prior to testing. Rats were first assigned to either a treatment or control group (N=8), then weighed, administered drug or vehicle orally, and returned to their home cage. Thirty minutes later, food was made available to the animals. The the food and the food hopper was weighed before, one hour, two hours, and four hours after food was made available to the test animals. Weight of food consumed plus spillage by the treatment animals was compared to food consumed plus spillage by control animals using a one-way ANOVA, with a Dunnett's post-hoc test.

Representative compounds of the present invention were tested in the feeding assay and were found to reduce food consumed by fasting rats.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See, e.g., REMINGTON'S PHARMACEUTICAL SCIENCES, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

FORMULATION EXAMPLE 1

Hard gelatin capsules containing the following ingredients are prepared:

| Ingredient | Quantity (mg/capsule) |
| --- | --- |
| Compound of Example 10 | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
| --- | --- |
| Compound of Example 11 | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
| --- | --- |
| Compound of Example 12 | 5 |
| Lactose | 95 |

The active mixture is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
| --- | --- |
| Compound of Example 76 | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
|---|---|
| Compound of Example 50 | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
|---|---|
| Compound of Example 59 | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 ml dose are made as follows:

| Ingredient | Amount |
|---|---|
| Compound of Example 74 | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

Capsules, each containing 15 mg of medicament, are made as follows:

| Ingredient | Quantity (mg/capsule) |
|---|---|
| Compound of Example 17 | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

FORMULATION EXAMPLE 9

An intravenous formulation may be prepared as follows:

| Ingredient | Quantity |
|---|---|
| Compound of Example 39 | 250.0 mg |
| Isotonic saline | 1000 ml |

FORMULATION EXAMPLE 10

A topical formulation may be prepared as follows:

| Ingredient | Quantity |
|---|---|
| Compound of Example 42 | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

FORMULATION EXAMPLE 11

Sublingual or buccal tablets, each containing 10 mg of active ingredient, may be prepared as follows:

| Ingredient | Quantity Per Tablet |
|---|---|
| Compound of Example 57 | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

We claim:

1. The compounds of Formula I:

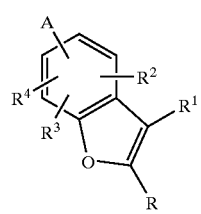

where:

A is a piperazine of formula:

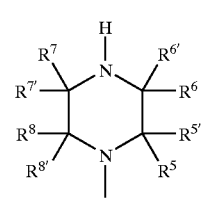

R is hydrogen, halo, trifluoromethyl or $C_1$–$C_6$ alkyl;

$R^1$ is hydrogen, halo, trifluoromethyl, phenyl, or $C_1$–$C_6$ alkyl;

$R^2$, $R^3$, and $R^4$ are independently hydrogen, halo, dihalomethyl, trifluoromethyl, 1,1-difluoroethy-1-yl, cyano, $C_1$–$C_4$ alkoxy, $C_1$–$C_4$ alkoxycarbonyl, $C_1$–$C_6$ alkyl, $C_1$–$C_6$ alkyl, —C(O)NHR$^9$, or $C_1$–$C_6$ alkyl substituted with a substituent selected from the group consisting of halo, $C_1$–$C_4$ alkoxy and hydroxy;

$R^5$, $R^6$, $R^7$ and $R^8$ are independently hydrogen, phenyl, benzyl, hydroxymethyl, halomethyl, dihalomethyl, trihalomethyl, or benzyloxymethyl;

$R^{5'}$ is hydrogen or methyl, provided that $R^{5'}$ may be methyl only when $R^5$ is other than hydrogen;

$R^{6'}$ is hydrogen or methyl, provided that $R^{6'}$ may be methyl only when $R^6$ is other than hydrogen;

$R^{7'}$ is hydrogen or methyl, provided that $R^{7'}$ may be methyl only when $R^7$ is other than hydrogen;

$R^{8'}$ is hydrogen or methyl, provided that $R^{8'}$ may be methyl only when $R^8$ is other than hydrogen;

$R^9$ is $C_1$–$C_8$ alkyl where the alkyl chain is optionally substituted with a substituent selected from the group consisting of phenyl and pyridyl;

or pharmaceutically acceptable acid addition salts thereof subject to the following provisos:

a) when $R^2$, $R^3$, and $R^4$ are all selected from the group consisting of hydrogen, trifluoromethyl, cyano, $C_1$–$C_4$ alkoxy, or $C_1$–$C_4$ alkyl, neither $R^6$ nor $R^7$ may be hydrogen unless:
1. R is halo;
2. $R^1$ is halo or phenyl;
3. $R^5$ or $R^8$ are other than hydrogen;

b) at least one of $R^5$, $R^6$, $R^7$, or $R^8$ must be other than hydrogen;

c) when $R^1$ is bromo or R is methyl, at least one of $R^2$, $R^3$, and $R^4$ must be other than hydrogen; and d) no more than two of $R^5$, $R^6$, $R^7$, and $R^8$ may be other than hydrogen.

2. A pharmaceutical formulation which comprises, in association with a pharmaceutically acceptable carrier, diluent or excipient, a compound of Formula I:

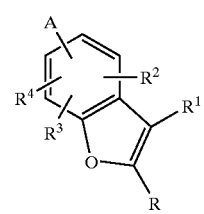

where:

A is a piperazine of formula:

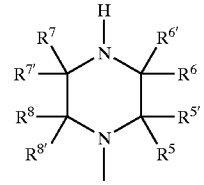

(i)

R is hydrogen, halo, trifluoromethyl or $C_1$–$C_6$ alkyl;

$R^1$ is hydrogen, halo, trifluoromethyl, phenyl, or $C_1$–$C_6$ alkyl;

$R^2$, $R^3$, and $R^4$ are independently hydrogen, halo, dihalomethyl, trifluoromethyl, 1,1-difluoroethy-1-yl, cyano, $C_1$–$C_4$ alkoxy, $C_1$–$C_4$ alkoxycarbonyl, $C_1$–$C_6$ alkyl, $C_1$–$C_6$ alkyl, —C(O)NHR$^9$, or $C_1$–$C_6$ alkyl substituted with a substituent selected from the group consisting of halo, $C_1$–$C_4$ alkoxy and hydroxy;

$R^5$, $R^6$, $R^7$ and $R^8$ are independently hydrogen, phenyl, benzyl, hydroxymethyl, halomethyl, dihalomethyl, trihalomethyl, or benzyloxymethyl;

$R^{5'}$ is hydrogen or methyl, provided that $R^{5'}$ may be methyl only when $R^5$ is other than hydrogen;

$R^{6'}$ is hydrogen or methyl, provided that $R^{6'}$ may be methyl only when $R^6$ is other than hydrogen;

$R^{7'}$ is hydrogen or methyl, provided that $R^{7'}$ may be methyl only when $R^7$ is other than hydrogen;

$R^{8'}$ is hydrogen or methyl, provided that $R^{8'}$ may be methyl only when $R^8$ is other than hydrogen;

$R^9$ is $C_1$–$C_8$ alkyl where the alkyl chain is optionally substituted with a substituent selected from the group consisting of phenyl and pyridyl;

or pharmaceutically acceptable acid addition salts thereof subject to the following provisos:

a) when $R^2$, $R^3$, and $R^4$ are all selected from the group consisting of hydrogen, trifluoromethyl, cyano, $C_1$–$C_4$ alkoxy, or $C_1$–$C_4$ alkyl, neither $R^6$ nor $R^7$ may be hydrogen unless:

1. R is halo;
2. $R^1$ is halo or phenyl;
3. $R^5$ or $R^8$ are other than hydrogen;

b) at least one of $R^5$, $R^6$, $R^7$, or $R^8$ must be other than hydrogen;

c) when $R^1$ is bromo or R is methyl, at least one of $R^2$, $R^3$, and $R^4$ must be other than hydrogen; and d) no more than two of $R^5$, $R^6$, $R^7$, and $R^8$ may be other than hydrogen.

3. A method for the treatment of obesity in mammals, comprising administering to a mammal in need of such activation a pharmaceutically effective amount of a compound of Formula I:

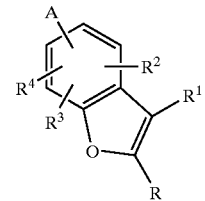

I where:

A is a piperazine of formula:

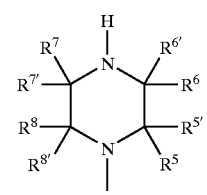

(i)

R is hydrogen, halo, trifluoromethyl or $C_1$–$C_6$ alkyl;

$R^1$ is hydrogen, halo, trifluoromethyl, phenyl, or $C_1$–$C_6$ alkyl;

$R^2$, $R^3$, and $R^4$ are independently hydrogen, halo, dihalomethyl, trifluoromethyl, 1,1-difluoroethy-1-yl, cyano, $C_1$–$C_4$ alkoxy, $C_1$–$C_4$ alkoxycarbonyl, $C_1$–$C_6$ alkyl, $C_1$–$C_6$ alkyl, —C(O)NHR$^9$, or $C_1$–$C_6$ alkyl substituted with a substituent selected from the group consisting of halo, $C_1$–$C_4$ alkoxy and hydroxy;

$R^5$, $R^6$, $R^7$ and $R^8$ are independently hydrogen, $C_1$–$C_6$ alkyl, phenyl, benzyl, hydroxymethyl, halomethyl, dihalomethyl, trihalomethyl, or benzyloxymethyl;

$R^{5'}$ is hydrogen or methyl, provided that $R^{5'}$ may be methyl only when $R^5$ is other than hydrogen; or $R^5$ and $R^{5'}$, together with the carbon atom to which they are attached, form a cyclopropyl moiety;

$R^{6'}$ is hydrogen or methyl, provided that $R^{6'}$ may be methyl only when $R^6$ is other than hydrogen; or $R^6$ and $R^{6'}$, together with the carbon atom to which they are attached, form a cyclopropyl moiety;

$R^{7'}$ is hydrogen or methyl, provided that $R^{7'}$ may be methyl only when $R^7$ is other than hydrogen; or $R^7$ and $R^{7'}$, together with the carbon atom to which they are attached, form a cyclopropyl moiety;

$R^{8'}$ is hydrogen or methyl, provided that $R^{8'}$ may be methyl only when $R^8$ is other than hydrogen; or $R^8$ and $R^{8'}$, together with the carbon atom to which they are attached, form a cyclopropyl moiety;

$R^9$ is $C_1$–$C_8$ alkyl where the alkyl chain is optionally substituted with a substituent selected from the group consisting of phenyl and pyridyl;

or pharmaceutically acceptable acid addition salts thereof subject to the following provisos:

a) when $R^2$, $R^3$, and $R^4$ are all selected from the group consisting of hydrogen, trifluoromethyl, cyano, $C_1$–$C_4$ alkoxy, or $C_1$–$C_4$ alkyl, neither $R^6$ nor $R^7$ may be selected from the group consisting of hydrogen and $C_1$–$C_6$ alkyl unless:

1. R is halo;
2. $R^1$ is halo or phenyl;
3. $R^5$ or $R^8$ are other than hydrogen;

b) when R, $R^1$, and two of $R^2$, $R^3$, and $R^4$ are hydrogen and one of $R^2$, $R^3$, or $R^4$ is selected from the group consisting of fluoro, chloro, bromo, methyl, or methoxy, at least one of $R^5$, $R^6$, $R^7$, or $R^8$ must be other than hydrogen;

c) when $R^1$ is bromo or R is methyl, at least one of $R^2$, $R^3$, and $R^4$ must be other than hydrogen; and d) no more than two of $R^5$, $R^6$, $R^7$, and $R^8$ may be other than hydrogen.

4. The method of claim 3 where the mammal is human.

5. A method for the treatment of obsessive compulsive disorder in mammals, comprising administering to a mammal in need of such treatment an effective amount of a compound of Formula I of claim 1, or a pharmaceutically acceptable acid addition salt thereof.

6. The method of claim 5 where the mammal is human.

7. A compound of claim 1 where A is attached at either the 4- or 7-position of the benzofuran nucleus.

8. A compound of claim 7 where A is attached at the 7-position of the benzofuran nucleus.

9. A compound according to claim 8 where $R^2$, $R^3$, $R^4$ are selected from the group consisting of hydrogen, halo, difluoromethyl, or trifluoromethyl.

* * * * *